United States Patent
Khoury et al.

(10) Patent No.: US 9,839,723 B2
(45) Date of Patent: *Dec. 12, 2017

(54) METHODS FOR IMPROVING THE BIOACTIVITY CHARACTERISTICS OF A SURFACE AND OBJECTS WITH SURFACES IMPROVED THEREBY

(71) Applicant: Exogenesis Corporation, Billerica, MA (US)

(72) Inventors: Joseph Khoury, Dedham, MA (US); Laurence B. Tarrant, Beverly Farms, MA (US); Sean R. Kirkpatrick, Littleton, MA (US); Richard C. Svrluga, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/130,354

(22) Filed: Apr. 15, 2016

(65) Prior Publication Data

US 2016/0228609 A1   Aug. 11, 2016

Related U.S. Application Data

(62) Division of application No. 14/238,774, filed as application No. PCT/US2012/051887 on Aug. 22, 2012, now Pat. No. 9,315,798.

(60) Provisional application No. 61/526,134, filed on Aug. 22, 2011.

(51) Int. Cl.
| | |
|---|---|
| *A61L 27/38* | (2006.01) |
| *A61L 27/18* | (2006.01) |
| *A61L 27/06* | (2006.01) |
| *A61L 27/16* | (2006.01) |
| *A61L 27/50* | (2006.01) |
| *C12N 13/00* | (2006.01) |

(52) U.S. Cl.
CPC .............. *A61L 27/38* (2013.01); *A61L 27/06* (2013.01); *A61L 27/16* (2013.01); *A61L 27/18* (2013.01); *A61L 27/50* (2013.01); *C12N 13/00* (2013.01); *A61L 2300/64* (2013.01); *A61L 2400/18* (2013.01)

(58) Field of Classification Search
None
See application file for complete search history.

(56) References Cited

U.S. PATENT DOCUMENTS

| | | | |
|---|---|---|---|
| 4,775,789 A | 10/1988 | Albridge, Jr. et al. | |
| 4,935,623 A * | 6/1990 | Knauer ..................... | H05H 3/02 118/715 |
| 5,018,847 A | 5/1991 | Ojima et al. | |
| 5,527,731 A | 6/1996 | Yamamoto et al. | |
| 5,607,480 A * | 3/1997 | Beaty ..................... | A61C 8/0012 623/23.5 |
| 5,669,935 A | 9/1997 | Rosenman et al. | |
| 5,707,684 A | 1/1998 | Hayes et al. | |
| 5,770,123 A | 6/1998 | Hatakeyama et al. | |
| 5,895,419 A | 4/1999 | Tweden et al. | |
| 5,998,097 A | 12/1999 | Hatakeyama et al. | |
| 6,331,227 B1 | 12/2001 | Dykstra et al. | |
| 6,486,478 B1 | 11/2002 | Libby et al. | |
| 6,491,800 B2 | 12/2002 | Kirkpatrick et al. | |
| 6,613,240 B2 | 9/2003 | Skinner et al. | |
| 6,635,883 B2 | 10/2003 | Torti et al. | |
| 6,646,277 B2 | 11/2003 | Mack et al. | |
| 6,676,989 B2 | 1/2004 | Kirkpatrick et al. | |
| 6,863,786 B2 | 3/2005 | Blinn et al. | |
| 7,060,989 B2 | 6/2006 | Swenson et al. | |
| 7,105,199 B2 | 9/2006 | Blinn et al. | |
| 7,115,511 B2 | 10/2006 | Hautala | |
| 7,247,845 B1 | 7/2007 | Gebhardt et al. | |
| 7,431,959 B1 | 10/2008 | Dehnad | |
| 2001/0054686 A1 | 12/2001 | Torti et al. | |
| 2002/0017455 A1 | 2/2002 | Kirkpatrick et al. | |
| 2002/0115208 A1 | 8/2002 | Mitchell et al. | |
| 2002/0188324 A1 * | 12/2002 | Blinn ..................... | A61L 31/14 607/3 |
| 2003/0021908 A1 | 1/2003 | Nickel et al. | |
| 2003/0026990 A1 | 2/2003 | Yamada et al. | |
| 2004/0112866 A1 | 6/2004 | Maleville et al. | |
| 2005/0112881 A1 | 5/2005 | Prakash et al. | |
| 2005/0220848 A1 | 10/2005 | Bates | |
| 2006/0019408 A1 | 1/2006 | Waggoner et al. | |

(Continued)

FOREIGN PATENT DOCUMENTS

| | | |
|---|---|---|
| EP | 0174180 B1 | 8/1989 |
| WO | 2005046746 A2 | 5/2005 |

(Continued)

OTHER PUBLICATIONS

Ito, Y. Surface micropatterning to regulate cell functions. Biomaterials (1999), vol. 20, pp. 2333-2342.
Castner, D.G. et al. Biomedical surface science: Foundations to frontiers. Surface Science (2002), vol. 500, pp. 28-60.
Loh, J. H. Plasma surface modification in biomedical applications. Med Device Technol. (1999) vol. 10(1), pp. 24-30.
Yamada, I. et al. Materials processing by gas cluster ion beams. Materials Science and Engineering (2001) vol. 34, pp. 231-295.
Yu, Q.S. et al. Surface modification of poly(tetrafluoroethylene) by a low-temperature cascade arc torch and radio-frequency plasmas. J. of Polymer Science Part A: Polymer Chemistry, 37(23), 4432-4441, Dec. 1, 1999.

(Continued)

*Primary Examiner* — H. Sarah Park
(74) *Attorney, Agent, or Firm* — Burns & Levinson LLP; Jerry Cohen; David Gomes

(57) ABSTRACT

A method for improving bioactivity of a surface of an implantable object comprising titania, titanium, an alloy of titanium, and/or polytetrafluoroethylene (PTFE) and implantable objects prepared thereby provides forming an accelerated neutral beam derived from an accelerated gas-cluster ion-beam (GCIB) in a reduced-pressure chamber, introducing an implantable object into the reduced-pressure chamber, and irradiating at least a first portion of the surface of said implantable object with a GCIB-derived neutral beam.

13 Claims, 19 Drawing Sheets

(56) References Cited

U.S. PATENT DOCUMENTS

| | | | |
|---|---|---|---|
| 2006/0043317 A1 | 3/2006 | Ono et al. | |
| 2006/0097185 A1 | 5/2006 | Mack | |
| 2006/0204534 A1 | 9/2006 | Blinn et al. | |
| 2006/0278611 A1 | 12/2006 | Sato et al. | |
| 2007/0029500 A1 | 2/2007 | Coulombe et al. | |
| 2007/0185488 A1 | 8/2007 | Pohjonen et al. | |
| 2008/0124372 A1 | 5/2008 | Hossainy et al. | |
| 2009/0017438 A1 | 1/2009 | Roy et al. | |
| 2009/0024229 A1 | 1/2009 | Chen et al. | |
| 2009/0032725 A1 | 2/2009 | Hautala | |
| 2009/0053278 A1 | 2/2009 | Fatora et al. | |
| 2009/0074834 A1* | 3/2009 | Kirkpatrick | B05D 3/068 424/423 |
| 2009/0140165 A1 | 6/2009 | Hautala et al. | |
| 2009/0198264 A1 | 8/2009 | Svrluga et al. | |
| 2010/0016985 A1 | 1/2010 | Rabiei | |
| 2010/0137674 A1 | 6/2010 | Evans et al. | |
| 2010/0227523 A1 | 9/2010 | Khoury et al. | |
| 2012/0100571 A1 | 4/2012 | Stupp et al. | |

FOREIGN PATENT DOCUMENTS

| | | |
|---|---|---|
| WO | 2007126411 A2 | 11/2007 |
| WO | 2010/105102 A1 | 9/2010 |
| WO | 2011/140332 A1 | 11/2011 |

OTHER PUBLICATIONS

Wegner, K. et al. (2006), "Gas-phase synthesis of nanostructured particulate films", KONA Powder and Particle, 24, 54-69.

Toyoda, N. et al. Cluster size dependence on energy and velocity distributions of gas cluster ions after collisions with residual gas. Nuclear Instruments and Methods in Physics Research Section B: Beam Interactions with Materials and Atoms, vol. 257, Issues 1-2, Apr. 2007, pp. 662-665.

Swenson, D.R. Measurement of averages of charge, energy and mass of large, multiply charged cluster ions colliding with atoms. Nuclear Instruments and Methods in Physics Research Section B: Beam Interactions with Materials and Atoms, vol. 222, Issues 1-2, Jul. 2004, pp. 61-67.

Houzumi, S. et al. Scanning Tunneling Microscopy Observation of Graphite Surfaces Irradiated with Size-Selected Ar Cluster Ion Beams, (2005) Jpn. J. Appl. Phys. 44(8), 6252-6254.

International Search Report dated Nov. 16, 2012 for PCT/US12/51887.

International Preliminary Report on Patentability dated Feb. 25, 2014 for PCT/US12/51887.

Japanese Patent Application S.N. 221411-527266 office action from Japan Patent Office dated May 24, 2016 and translation.

* cited by examiner

METHODS FOR IMPROVING THE BIOACTIVITY CHARACTERISTICS OF A SURFACE AND OBJECTS WITH SURFACES IMPROVED THEREBY

CROSS-REFERENCE TO RELATED APPLICATIONS

This application is a divisional of co-pending U.S. patent application Ser. No. 14/238,774, filed on Apr. 28, 2014, and entitled METHODS FOR IMPROVING THE BIOACTIVITY CHARACTERISTICS OF A SURFACE AND OBJECTS WITH SURFACES IMPROVED THEREBY, which in turn is a U.S. national stage application under 35 U.S.C. 371 of International Application No. PCT/US2012/051887, filed on Aug. 22, 2012, which in turn claims priority to and benefit of U.S. Provisional Patent Application No. 61/526,134, filed on Aug. 22, 2011, the contents of which are incorporated by reference herein in their entirety for all purposes.

FIELD OF THE INVENTION

This invention relates generally to methods for improving the bioactivity characteristics of a surface of an object and to production of objects having at least a portion of a surface with improved bioactivity. More specifically, it relates to methods for improving a surface by increasing its bioactivity through the use of gas cluster ion beam technology and/or through the use of a neutral gas cluster beam and/or neutral monomer beam.

BACKGROUND OF THE INVENTION

It is often desirable that an object will have a surface that has an increased ability to attract and host the growth, attachment and proliferation of living biological cells. This is often the case for certain biological laboratory wares, including for example, tissue culture dishes, flasks and roller flasks, wells and chamber slides, plates, Petri dishes, etc. It is also often the case for medical objects intended for implant, including sutures, and also for environmental testing devices used to test airborne or waterborne contaminants.

As used herein, the term "bioactivity," used in relation to a surface or an object or portion of an object, is intended to mean suitability of the surface or object or object portion for attracting living cells and/or tissues, including bone, or fluids thereto, or for improving cell and/or tissue activity thereon, or for attaching living cells thereto, or for promoting growth of living cells thereon, or for promoting proliferation of living cells thereon. Living cells, tissues and fluids include such materials presently or recently alive and extracted from or within a mammal (including human) or synthetic simulations thereof. As used herein the term "titania" is intended to include oxides of titanium in all forms including ceramic forms, and the titanium metal itself (or an alloy thereof) together with a surface coating of native oxide or other oxide comprising the element titanium (including without limitation $TiO_2$, and or $TiO_2$ with imperfect stoichiometry). Implantable medical devices are often fabricated from titanium metal (or alloy) that typically has a titania surface (which may be either a native oxide, or a purposely oxidized surface, or otherwise).

As used herein, the term "drug" is intended to mean a therapeutic agent or a material (including small molecule pharmaceutical drugs and larger biologics) that is active in a generally beneficial way, which can be released or eluted locally in the vicinity of an implantable medical device to facilitate implanting (for example, without limitation, by providing lubrication) the device, or to facilitate (for example, without limitation, through biological or biochemical activity) a favorable medical or physiological outcome of the implantation of the device. The meaning of "drug" is intended to include a mixture of a drug with a polymer that is employed for the purpose of binding or providing coherence to the drug, attaching the drug to the medical device, or for forming a barrier layer to control release or elution of the drug. A drug that has been modified by ion beam irradiation to densify, carbonize or partially carbonize, partially denature, cross-link or partially cross-link, or to at least partially polymerize molecules of the drug is intended to be included in the "drug" definition.

As used herein, use of the term "suture" (as a noun) is intended to include ligatures and other fibers, filaments, or threads used for the surgical closure of wounds, for the control of hemorrhage, or for the surgical joining or retaining of tendons, ligaments, cartilage, bone and/or other tissues.

As used herein, the term "intermediate size", when referring to gas cluster size or gas cluster ion size is intended to mean sizes of from N=10 to N=1500. Where N signifies the number of monomers comprising the gas cluster or gas cluster ion.

As used herein, the term "monomer" refers equally to either a single atom or a single molecule. The terms "atom," "molecule," and "monomer" may be used interchangeably and all refer to the appropriate monomer that is characteristic of the gas under discussion (either a component of a cluster, a component of a cluster ion, or an atom or molecule). For example, a monatomic gas like argon may be referred to in terms of atoms, molecules, or monomers and each of those terms means a single atom. Likewise, in the case of a diatomic gas like nitrogen, it may be referred to in terms of atoms, molecules, or monomers, each term meaning a diatomic molecule. Furthermore a molecular gas like $CO_2$, may be referred to in terms of atoms, molecules, or monomers, each term meaning a three atom molecule, and so forth. These conventions are used to simplify generic discussions of gases and gas clusters or gas cluster ions independent of whether they are monatomic, diatomic, or molecular in their gaseous form.

Biological laboratory wares may be employed in cell culture, tissue culture, explant culture, and tissue engineering applications (for examples) and is commonly formed from generally inert and/or biocompatible materials like glass, quartz, plastics and polymers, and certain metals and ceramics. It is often desirable to be able to modify at least a portion of the surface of such biological laboratory wares to enhance their bioactivity.

Medical objects intended for implant into the body or bodily tissues of a mammal (including human), as for example medical prostheses or surgical implants or grafts, may be fabricated from a variety of materials including, but not limited to, various metals, metal alloys, plastic or polymer or co-polymer materials (including, without limitation, woven, knitted, and non-woven polymeric/co-polymeric fabrics and solid materials such as polyether ether ketone (PEEK)), solid resin materials, glass and glassy materials, biological materials such as bone and collagen, silk and other natural fibers, and other materials (including without limitation, poly[glutamic acid], poly[lactic-co-glycolic acid], and poly[L-lactide]) that may be suitable for the application and that are appropriately biocompatible. As examples, certain stainless steel alloys, titanium and titanium alloys (including possible native oxide coatings), cobalt-chrome alloys, cobalt-chrome-molybdenum alloy, tantalum, tantalum alloys, zirconium, zirconium alloys (including possible native oxide coatings), polyethylene and other inert plastics, and various ceramics including titania, alumina, and zirconia ceramics are employed. Polymeric/co-polymeric fabrics may for example be formed from polyesters (including polyethylene terephthalate (PETE)), polytetrafluoroethylene (PTFE), aramid, polyamide or other suitable fibers. Medical objects intended for implant include for example, without limitation, vascular stents, vascular and other grafts, dental implants, artificial and natural joint prostheses, coronary pacemakers, implantable lenses, etc. and components thereof. Often such a device may have a native surface state with cellular adhesion and cellular proliferation properties that are less than ideal for the intended purpose. In such cases it is often desirable to be able to modify at least a portion of the surface of the object to enhance cellular attachment thereto in order to make it more suitable for the implant application.

During ligament or tendon repair, a common surgical approach is to suture the damaged site with or without the use of a suture anchor and to allow healing to occur spontaneously, typically over an extended period of time. An issue acing ligament and tendon repair is the lack of vascularity in the region, which decreases the potential of circulating stem cells to adhere to the repair site and aid in healing. By delivering mesenchymal stem cells (MSC) or osteoblasts to the region, a potential for enhanced healing occurs and healing time may be significantly decreased. Seeding MSC or osteoblasts onto a suture to deliver the cells to the region of repair is an advantage. However, seeding and attachment of MSC onto prior art commercially available sutures intended for ligament and tendon repair is often difficult and requires the use of pre-coating the sutures with proteins or attachment factors such as, for example, collagen, fibrin, or poly-L-lysine, and often results are not as beneficial as may be desired. Alternative effective methods are desirable.

Environmental testing devices often include materials such as metals, plastics and polymers, glasses and quartz, etc.

During the past decade, gas cluster ion beams (GCIB) have become well known and widely used for a variety of surface and subsurface processing applications. Because gas cluster ions typically have a large mass, they tend to travel at relatively low velocities (compared to conventional ions) even when accelerated to substantial energies. These low velocities, combined with the inherently weak binding of the clusters, result in unique surface processing capabilities that lead to reduced surface penetration and reduced surface damage compared to conventional ion beams and diffuse plasmas.

Gas cluster ion beams have been employed to smooth, etch, clean, form deposits on, or otherwise modify a wide variety of surfaces. Because of the ease of forming GCIBs using argon gas and because of the inert properties of argon, many applications have been developed for processing the surfaces of implantable medical devices such as coronary stents, orthopedic prostheses, and other implantable medical devices using argon gas GCIBs. For example, U.S. Pat. No. 6,676,989C1 of Exogenesis Corporation issued to Kirkpatrick et al. teaches a GCIB processing system having a holder and manipulator suited for processing tubular or cylindrical workpieces such as vascular stents. In another example, U.S. Pat. No. 6,491,800B2 of Exogenesis Corporation issued to Kirkpatrick et al. teaches a GCIB processing system having workpiece holders and manipulators for processing other types of non-planar medical devices, including for example, hip joint prostheses. In still another example, U.S. Pat. No. 7,105,199B2 of Exogenesis Corporation issued to Blinn et al. teaches the use of GCIB processing to improve the adhesion of drug coatings on stents and to modify the elution or release rate of the drug from the coatings.

Gas cluster ion beam (GCIB) irradiation has been used for nano-scale modification of surfaces. In the commonly held published US patent publication 2009/0074834A1, "Method and System for Modifying the Wettability Characteristics of a Surface of a Medical Device by the Application of Gas Cluster Ion Beam Technology and Medical Devices Made Thereby," GCIB irradiation has been shown to modify the hydrophilic properties of non-biological material surfaces. It is generally known that cells, including but not limited to, anchorage-dependent cells such as fibroblasts and osteoblasts prefer hydrophilic surfaces to attach, grow, or differentiate well and they also prefer charged surfaces at physiological pH. Many methods have been employed to increase hydrophilicity or alter charge on non-biological surfaces, such as sandblasting, acid etching, sandblasting plus acid etching (SLA), plasma spraying of coatings, $CO_2$ laser smoothing and various forms of cleaning, including mechanical, ultrasonic, plasma, and chemical cleaning techniques. Other approaches have included the addition of surfactants or the application of films or coatings having different wettability characteristics. Various methods have also been employed to increase cell adherence properties of surfaces such as UV treatment, UV and ozone treatment, covalently attaching poly(ethylene glycol) (PEG), and the application of protein products such as the antibody anti-CD34 and arginine-glycine-aspartate peptides (RGD peptides).

Ions have long been favored for many processes because their electric charge facilitates their manipulation by electrostatic and magnetic fields. This introduces great flexibility in processing. However, in some applications, often including the processing of drugs, biological materials, and electrically insulating materials the charge that is inherent to any ion (including, but not limited to, charged gas cluster ions in a GCIB) may in some cases produce undesirable effects in the processed surfaces. GCIB has a distinct advantage over conventional ion beams in that a gas cluster ion with a single or small multiple charge enables the transport and control of a much larger mass-flow (a cluster may consist of hundreds or thousands of molecules) compared to a conventional ion (a single atom, molecule, or molecular fragment.) Particularly in the case of insulating materials, ion beam processed surfaces often suffer from charge induced damage resulting from abrupt discharge of accumulated charges, or production of damaging electrical field-induced stress in the material (again resulting from accumulated charges.) In such cases, GCIBs have an advantage due to their relatively low charge per mass, but may not entirely eliminate the workpiece-charging problem in many instances. Furthermore, moderate to high current intensity ion beams may suffer from a significant space charge-induced defocusing of the beam that tends to inhibit transmitting a well-focused beam over long distances. Again, because of their lower charge per mass, charged GCIBs have an advantage in this respect, but the space charge transport effects are not fully eliminated.

A further instance of need or opportunity arises from the fact that although the use of beams of neutral molecules or atoms provides benefit in some surface processing applications and in space charge-free beam transport, it has generally not been easy or economical to produce intense beams of neutral molecules or atoms except for the case of jets, where the energies are generally on the order of a few milli-electron-volts per atom or molecule. Higher energies per particle can be beneficial or necessary in many applications, for example when it is desirable to break surface bonds to facilitate cleaning, etching, smoothing, deposition, surface chemistry effects or other surface modification. In such cases, energies of from an eV to a several tens of eV per particle (or even higher) can often be useful. Methods and apparatus for forming such Neutral Beams by first forming an accelerated charged GCIB and then neutralizing or arranging for neutralization of at least a fraction of the beam and separating the charged and uncharged fractions are disclosed herein. The Neutral Beams may consist of neutral gas clusters, neutral monomers, or combinations of both.

It is therefore an object of this invention to provide a surface and an object having at least a portion of its surface modified by GCIB processing to have improved bioactivity.

It is further an objective of this invention to provide methods of forming a surface or an object having at least a portion of its surface modified to have improved bioactivity by employing GCIB technology.

It is further an objective of this invention to provide methods of forming a surface or an object having at least a portion of its surface modified to have improved bioactivity by employing GCIB technology.

Another objective of this invention is to provide a surface and an object having at least a portion of its surface modified to have improved bioactivity by employing Neutral Beam technology, wherein the Neutral Beam comprises gas clusters, monomers, or a combination of monomers and gas clusters.

A further objective of this invention is to provide a surface and an object having at least a portion of its surface modified to have improved bioactivity by employing Neutral Beam technology, wherein the Neutral Beam comprises gas clusters, monomers, or a combination of monomers and gas clusters derived from an accelerated gas cluster ion beam.

Still another objective of this invention is to provide methods for modifying a surface or at least a portion of a surface of an object with improved bioactivity by employing Neutral Beam technology, wherein the Neutral Beam comprises gas clusters, monomers, or a combination of monomers and gas clusters.

Yet another objective of this invention is to provide an object for medical implantation having at least a portion of its surface modified by GCIB processing and having cells attached in vitro prior to medical implantation.

A still further objective of this invention is to provide methods of forming an object for medical implantation having at least a portion of its surface modified by GCIB technology and by in vitro attachment of cells prior to medical implantation.

SUMMARY OF THE INVENTION

The objects set forth above as well as further and other objects and advantages of the present invention are achieved by the invention described herein below.

One of the fundamental challenges in tissue engineering has been the ability to allow cells from different lineages to grow and interact in a manner seen in the human body. GCIB irradiation of surfaces greatly improves cell adherence and proliferation while maintaining cellular differentiation. Wound repair in tissues and organs derived from epithelial, endothelial, mesenchymal, or neuronal cells can benefit when they are grown on inert or bio-active material that has been surface modified by GCIB irradiation. Whether the goal is to achieve integration between underlying bone and a dental implant; cellular infiltration and integration between a ligament and the attaching bone; enhancing skin or hair graft integration; or nerve regeneration to re-initiate synapses, the use of GCIB irradiation is a useful process in the progression of tissue engineering and wound repair.

The present invention is directed to the use of GCIB and/or Neutral Beam processing to form surface regions on objects intended for cellular attachment, the surface regions having improved bioactivity properties to facilitate growth, attachment and/or proliferation of cells. It is also directed to the in vitro attachment of cells to the GCIB processed surface regions of medical objects prior to medical/surgical implantation. The attached cells may be derived from the body of the individual for whom the medical/surgical implant is intended or may be derived from other compatible sources.

When it is intended that certain selected portions of the surface of the object intended for cell attachment should have improved bioactivity properties, and when it is intended that other portions of the surface of the object not be involved in cell attachment processes, GCIB processing may be limited to the selected portions by limiting the GCIB processing to only the selected portions of the surface of the object to increase the bioactivity properties for only the selected portions. Controlling the GCIB cross-sectional area and/or controlling the scanning and/or deflecting of the GCIB to limit the extent of its irradiation to only the selected surface portions may accomplish the limitation of GCIB processing to selected regions. Alternatively, conventional masking technology may be used to mask the surface portions for which GCIB processing is not desired, and to expose the selected surface portions for which GCIB processing is required. Subsequently the mask and the surface portions exposed through the mask may be irradiated with a diffuse or scanned GCIB. Various other methods of limiting the GCIB irradiation to selected regions of a surface or of the surface of an object will be known to those skilled in the art and are intended to be encompassed in the invention.

Beams of energetic conventional ions, accelerated electrically charged atoms or molecules, are widely utilized to form semiconductor device junctions, to modify surfaces by sputtering, and to modify the properties of thin films. Unlike conventional ions, gas cluster ions are formed from clusters of large numbers (having a typical distribution of several hundreds to several thousands with a mean value of a few thousand) of weakly bound atoms or molecules of materials that are gaseous under conditions of standard temperature and pressure (commonly oxygen, nitrogen, or an inert gas such as argon, for example, but any condensable gas can be used to generate gas cluster ions) with each cluster sharing one or more electrical charges, and which are accelerated together through high electric potential differences (on the order of from about 3 kV to about 70 kV or more) to have high total energies. After gas cluster ions have been formed and accelerated, their charge states may be altered or become altered (even neutralized), and they may fragment or may be induced to fragment into smaller cluster ions or into monomer ions and/or neutralized smaller clusters and neutralized monomers, but they tend to retain the relatively high velocities and energies that result from having been accelerated through high electric potential differences, with the energy being distributed over the fragments. After gas cluster ions have been formed and accelerated, their charge states may be altered or become altered (even neutralized)

by collisions with other cluster ions, other neutral clusters, or residual background gas particles, and thus they may fragment or may be induced to fragment into smaller cluster ions or into monomer ions and/or into neutralized smaller clusters and neutralized monomers, but the resulting cluster ions, neutral clusters, and monomer ions and neutral monomers tend to retain the relatively high velocities and energies that result from having been accelerated through high electric potential differences, with the accelerated gas cluster ion energy being distributed over the fragments.

Being loosely bound, gas cluster ions disintegrate upon impact with a surface and the total energy of the accelerated gas cluster ion is shared among the constituent atoms. Because of this energy sharing, the atoms in the clusters are individually much less energetic (after disintegration) than as is the case for conventional ions and, as a result, the atoms penetrate to much shallower depths, despite the high energy of the accelerated gas cluster ion. As used herein, the terms "GCIB", "gas cluster ion beam" and "gas cluster ion" are intended to encompass not only ionized beams and ions, but also accelerated beams and ions that have had all or a portion of their charge states modified (including neutralized) following their acceleration. The terms "GCIB" and "gas cluster ion beam" are intended to encompass all beams that comprise accelerated gas cluster ions even though they may also comprise non-clustered particles. As used herein, the term "Neutral Beam" is intended to mean a beam of neutral gas clusters and/or neutral monomers derived from an accelerated gas cluster ion beam and wherein the acceleration results from acceleration of a gas cluster ion beam.

Because the energies of individual atoms within a gas cluster ion are very small, typically a few eV to some tens of eV, the atoms penetrate through, at most, only a few atomic layers of a target surface during impact. This shallow penetration (typically a few nanometers to about ten nanometers, depending on the beam acceleration) of the impacting atoms means all of the energy carried by the entire cluster ion is consequently dissipated in an extremely small volume in a very shallow surface layer during a time period of less than a microsecond. This differs from conventional ion beams where the penetration into the material is sometimes several hundred nanometers, producing changes and material modification deep below the surface of the material. Because of the high total energy of the gas cluster ion and extremely small interaction volume, the deposited energy density at the impact site is far greater than in the case of bombardment by conventional ions. Accordingly, GCIB processing of a surface can produce modifications that can enhance properties of the surface to result in improved suitability for subsequent cell growth, attachment and proliferation.

When accelerated gas cluster ions are fully dissociated and neutralized, the resulting neutral monomers will have energies approximately equal to the total energy of the original accelerated gas cluster ion, divided by the number, $N_1$, of monomers that comprised the original gas cluster ion at the time it was accelerated. Such dissociated neutral monomers will have energies on the order of from about 1 eV to tens or even a few hundreds of eV, depending on the original accelerated energy of the gas cluster ion and the size of the gas cluster.

Without wishing to be bound to any particular theory, it is believed that the increased bioactivity observed for surfaces processed by GCIB irradiation or Neutral Beam irradiation according to the methods of the invention may result from a physical transformation of the structure of the GCIB irradiated surfaces.

Gas cluster ion beams are generated and transported for purposes of irradiating a workpiece according to known techniques. Various types of holders are known in the art for holding the object in the path of the GCIB for irradiation and for manipulating the object to permit irradiation of a multiplicity of portions of the object.

Neutral Beams are generated and transported for purposes of irradiating a workpiece according to techniques taught herein.

The objects having beam-improved surfaces according to the invention may be employed (for example, not for limitation) in biological laboratory wares intended for cell culture, tissue culture, explant culture, tissue engineering, or other cell attachment or growth applications) or may be medically/surgically implanted into or onto the body or bodily tissues of a mammal or other biological entity, or may be employed for environmental testing applications, etc. Optionally, objects may be additionally processed to effect in vitro attachment of cells onto the beam-processed surfaces prior to their application, as in for example, medical/surgical implantation.

In some embodiments of the invention, a method for deriving a high beam-purity neutral gas cluster and/or monomer beam from an accelerated gas cluster ion beam is employed. The neutral gas cluster and/or monomer beam may be employed for a variety of types of surface and shallow subsurface materials processing and is capable of superior performance compared to conventional GCIB processing for some applications. It can provide well-focused intense neutral monomer beams having energies in the range of from about 1 eV to about 100 eV (or even a few hundred eV.) This is an energy range in which it has heretofore been impractical with simple, relatively inexpensive apparatus to form intense neutral beams.

These Neutral Beams are formed by first forming a conventional accelerated GCIB, then partly or fully dissociating it by methods and operating conditions that do not introduce impurities into the beam, then separating the remaining charged portion of the beam from the neutral portion, and using the resulting Neutral Beam for workpiece processing. Depending on the degree of dissociation of the gas cluster ions, the Neutral Beam produced may be a mixture of neutral gas monomers and gas clusters or may consist essentially entirely of neutral gas monomers.

An advantage of the Neutral Beams that may be produced by the methods of this invention, is that they may be used to process materials that may be damaged or otherwise adversely affected by a charged ion beam, for example (without limitation) electrically insulating materials, without producing damage to the materials due to charging of the surfaces of such materials by beam transported charges as may occur with ionized beams. The use of Neutral Beams can enable successful beam processing of polymer, dielectric, and/or other electrically insulating or high electrical resistivity materials, coatings, and films in other applications where ion beams may produce unacceptable side effects due to surface or other charging effects. In other examples, Neutral Beam induced modifications of polymer or other dielectric materials (e.g. sterilization, smoothing, improved biocompatibility, and improved attachment of drugs) may enable the use of such materials in medical implant and other medical/surgical applications. Further examples include Neutral Beam processing of glass, polymer, and ceramic bio-culture labware and/or environmental sampling surfaces may be used to improve surface characteristics such as roughness, smoothness, hydrophilicity, and biocompatibility.

Since the original GCIB is charged, it is readily accelerated to desired energy and is readily focused, deflected, scanned or otherwise handled. Upon separating of the charged ions from the dissociated neutral beam components, the neutral beam particles tend to retain their initial trajectories and may be transported for extensive distances with good focus.

It is believed that gas cluster ions may dissociate for a variety of reasons, often by evaporation of monomers from the cluster ion. In the ionizer, incident accelerated electrons may transfer energy to the clusters as well as inducing cluster ionization. This energy transfer may leave the cluster in an excited state that may result in downstream evaporation of neutral monomers from the gas cluster ions. Alternatively, accelerated gas cluster ions may collide with residual gas molecules and/or other clusters. Such collisions may result in cluster fragmentation and/or energy transfer resulting in subsequent evaporation of neutral monomers from the gas cluster ions.

Because the dissociation is induced by collision with electrons or with gas molecules (and/or gas clusters) of the same gas from which the GCIB was formed, no contamination is contributed to the beam by the dissociation process.

There are several mechanisms that can be employed for dissociating gas cluster ions in a GCIB. Some of these mechanisms also act to dissociate neutral gas clusters in a neutral gas cluster beam. By depending entirely on collisions within the beam to produce dissociation, contamination of the beam by collision with other materials is avoided. As a neutral gas cluster jet from a nozzle travels through an ionizing region where electrons are induced to ionize the clusters, a cluster may remain un-ionized or may acquire a charge state of one or more charges (by ejection of electrons from the cluster by an incident electron). The ionizer operating conditions influence the likelihood that a gas cluster will take on a particular charge state, with more intense ionizer conditions resulting in greater probability that a higher charge state will be achieved. More intense ionizer conditions resulting in higher ionization efficiency may result from higher electron flux and/or higher (within limits) electron energy. Once the gas cluster has been ionized, it is typically extracted from the ionizer, focused into a beam, and accelerated by falling through an electric field. The amount of acceleration is readily controlled by controlling the magnitude of an accelerating electric field. Typical commercial GCIB processing tools generally provide for the gas cluster ions to be accelerated across an electric field having an adjustable accelerating potential, $V_{Acc}$, of from about 1 kV to 30 (or more) kV. Thus a singly charged gas cluster ion achieves an energy in the range of from 1 to 30 keV (or more) and a multiply charged (for example, without limitation, charge state, q=3 electronic charges) gas cluster ion achieves an energy in the range of from 3 to 90 keV (or more). For other gas cluster ion charge states and acceleration potentials, the accelerated energy per cluster is q times $V_{Acc}$. From a given ionizer with a given ionization efficiency, gas cluster ions will have a distribution of charge states from zero (not ionized) to a number that may be as high as 6 or more, and the peak of the charge state distribution increases with increased ionizer efficiency (higher electron flux and energy). Higher ionizer efficiency also results in increased numbers of gas cluster ions being formed in the ionizer. In many cases GCIB processing throughput increases when GCIB current is increased by operating the ionizer at high efficiency. A downside of such operation is that high charge states on intermediate size gas cluster ions can increase crater formation by those ions and often such crater formation may operate counterproductively to the intent of the processing. Thus for many GCIB surface processing recipes, selection of the ionizer operating parameters tends to involve more considerations than just maximizing beam current. In some processes, use of a "pressure cell" (see U.S. Pat. No. 7,060,989, to Swenson et al.) can be employed to permit operating an ionizer at high ionization efficiency while still obtaining acceptable beam processing performance by moderating the beam energy by gas collisions in an elevated pressure "pressure cell."

With the present invention there is no downside to operating the ionizer at high efficiency—in fact such operation is preferred. When the ionizer is operated at high efficiency, there may be a wide range of charge states in the gas cluster ions produced by the ionizer. This results in a wide range of velocities in the gas cluster ions in the extraction region between the ionizer and the accelerating electrode, and also in the downstream beam. This may result in an enhanced frequency of collisions between and among gas cluster ions in the beam that generally results in a higher degree of fragmentation of the largest gas cluster ions. Such fragmentation may result in a redistribution of the cluster sizes in the beam, skewing it toward the smaller cluster sizes. These cluster fragments retain energy in proportion to their new size (number N) and so become less energetic while essentially retaining the accelerated velocity of the initial unfragmented gas cluster ion. The change of energy with retention of velocity has been experimentally verified (as for example reported in Toyoda, N. et al., "Cluster size dependence on energy and velocity distributions of gas cluster ions after collisions with residual gas," Nucl. Instr. & Meth. In Phys. Research B 257 (2007), pp 662-665). Fragmentation may also result in redistribution of charges in the cluster fragments. Some uncharged fragments likely result and multicharged gas cluster ions may fragment into several charged gas cluster ions and perhaps some uncharged fragments. In the method of the Neutral Beam embodiments of the present invention, background gas pressure in the beamline may be arranged to have a higher pressure than is normally required for good GCIB transmission. When the pressure is arranged so that gas cluster ions have a short enough mean-free-path and a long enough flight path between ionizer and workpiece that they must undergo multiple collisions with background gas molecules. For a gas cluster ion containing N monomers and having a charge state of q and which has been accelerated through an electric field potential drop of V volts, the cluster will have an energy of approximately qV/N eV per monomer. Except for the smallest gas cluster ions, a collision of such an ion with a background gas monomer will result in deposition of approximately qV/N eV into the gas cluster ion. This energy is relatively small compared to the overall gas cluster ion energy and generally results in heating of the cluster and in evaporation of monomers from the cluster. It is believed that such collisions of larger clusters seldom fragment the cluster but rather warm them or result in evaporation of monomers. Such evaporated monomers have approximately the same energy qV/N eV and the approximately the same velocity as the gas cluster from which they have evaporated. When such evaporations occur from a gas cluster ion, the charge has a high probability of remaining with the residual gas cluster ion. Thus after a sequence of background gas collisions, a large gas cluster ion may be reduced to a cloud of co-traveling monomers with perhaps a small residual gas cluster ion. The co-traveling monomers all have approximately the same velocity as that of the original gas cluster ion and each has energy of approximately qV/N eV. For small gas cluster ions, the energy of collision with a background gas monomer is likely to completely and violently dissociate the small gas cluster and it is uncertain whether in such cases the resulting monomers continue to travel with the beam or are ejected from the beam.

Prior to the GCIB reaching the workpiece, the remaining charged particles (gas cluster ions, particularly small and intermediate size gas cluster ions and some charged monomers, but also including any remaining large gas cluster ions) in the beam are separated from the neutral beam components, leaving only the Neutral Beam to process the workpiece. For preferred operating conditions, the Neutral Beam has been measured to be comprised essentially entirely of neutral gas monomers.

In typical operation, the fraction of power in the neutral beam component relative to that in the fill (charged plus neutral) beam delivered at the processing target is in the range of from about 5% to 95%, so by the separation methods and apparatus of the present invention it is possible to deliver that portion of the kinetic energy of the full accelerated charged beam to the target as a Neutral Beam.

The dissociation of the gas cluster ions and thus the production of high neutral monomer beam flux is facilitated by 1) Operating at higher acceleration voltages. This increases qV/N for any given cluster size. 2) Operating at high ionizer efficiency. This increases qV/N for any given cluster size and increases cluster-ion on cluster-ion collisions in the extraction region; 3) Operating at a high beamline pressure or with a longer beam path, which increases the probability of background gas collisions for a gas cluster ion of any given size; and 4) Operating at higher nozzle gas flows, which increases transport of gas, clustered and perhaps unclustered into the GCIB trajectory. The product of the gas cluster ion beam path length from extraction region to workpiece times the pressure in that region determines the degree of dissociation of the gas cluster ions that occurs. For 30 kV acceleration, ionizer parameters that provide a mean gas cluster ion charge state of 1 or greater, and a pressure×beam path length of $6\times10^{-3}$ torr-cm (at 25° C.) provides a Neutral Beam (after separation from the residual charged ions) that is essentially fully dissociated to neutral energetic monomers. It is convenient and customary to characterize the product of pressure and beam path length as a gas target thickness. $6\times10^{-3}$ torr-cm corresponds to a gas target thickness of approximately $1.94\times10^{14}$ gas molecules per cm². In one exemplary (not for limitation) embodiment the background gas pressure is $6\times10^{-5}$ torr and the beam path length is 100 cm, the acceleration potential is 30 kV, and the Neutral Beam is observed to be essentially fully dissociated into monomers at the end of the beam path.

Measurement of the Neutral Beam cannot be made by current measurement as is convenient for gas cluster ion beams. A Neutral Beam power sensor is used to facilitate dosimetry when irradiating a workpiece with a Neutral Beam. The Neutral Beam sensor is a thermal sensor that intercepts the beam (or optionally a known sample of the beam). The rate of rise of temperature of the sensor is related to the energy flux resulting from energetic beam irradiation of the sensor. The thermal measurements must be made over a limited range of temperatures of the sensor to avoid errors due to thermal re-radiation of the energy incident on the sensor. For a GCIB process, the beam power (watts) is equal to the beam current (amps) times $V_{Acc}$, the beam acceleration voltage. When a GCIB irradiates a workpiece for a period of time (seconds), the energy (joules) received by the workpiece is the product of the beam power and the irradiation time. The processing effect of such a beam when it processes an extended area is distributed over the area (for example, cm²). For ion beams, it has been conveniently conventional to specify a processing dose in terms of irradiated ions/cm², where the ions are either known or assumed to have at the time of acceleration an average charge state, q, and to have been accelerated through a potential difference of $V_{Acc}$ volts, so that each ion carries an energy of q $V_{Acc}$ eV (an eV is approximately $1.6\times10^{-19}$ joule). Thus an ion beam dose for an average charge state, q, accelerated by $V_{Acc}$ and specified in ions/cm² corresponds to a readily calculated energy dose expressible in joules/cm². For an accelerated Neutral Beam derived from an accelerated GCIB as utilized in the present invention, the value of q at the time of acceleration and the value of $V_{Acc}$ is the same for both of the (later-formed and separated) charged and uncharged fractions of the beam. The power in the two (neutral and charged) fractions of the GCIB divides proportional to the mass in each beam fraction. Thus for the accelerated Neutral Beam as employed in the invention, when equal areas are irradiated for equal times, the energy dose (joules/cm²) deposited by the Neutral Beam is necessarily less than the energy dose deposited by the full GCIB. By using a thermal sensor to measure the power in the full GCIB $P_G$ and that in the Neutral Beam $P_N$ (which is commonly found to be about 5% to 95% that of the full GCIB) it is possible to calculate a compensation factor for use in the Neutral Beam processing dosimetry. When $P_N$ is $aP_G$, then the compensation factor is, k=1/a. Thus if a workpiece is processed using a Neutral Beam derived from a GCIB, for a time duration is made to be k times greater than the processing duration for the full GCIB (including charged and neutral beam portions) required to achieve a dose of D ions/cm², then the energy doses deposited in the workpiece by both the Neutral Beam and the full GCIB are the same (though the results may be different due to qualitative differences in the processing effects due to differences of particle sizes in the two beams.) As used herein, a Neutral Beam process dose compensated in this way is sometimes described as having an energy/cm² equivalence of a dose of D ions/cm².

Use of a Neutral Beam derived from a gas cluster ion beam in combination with a thermal power sensor for dosimetry in many cases has advantages compared with the use of the full gas cluster ion beam or an intercepted or diverted portion, which inevitably comprises a mixture of gas cluster ions and neutral gas clusters and/or neutral monomers, and which is conventionally measured for dosimetry purposes by using a beam current measurement. Some advantages are as follows:

1) The dosimetry can be more precise with the Neutral Beam using a thermal sensor for dosimetry because the total power of the beam is measured. With a GCIB employing the traditional beam current measurement for dosimetry, only the contribution of the ionized portion of the beam is measured and employed for dosimetry. Minute-to-minute and setup-to-setup changes to operating conditions of the GCIB apparatus may result in variations in the fraction of neutral monomers and neutral clusters in the GCIB. These variations can result in process variations that may be less controlled when the dosimetry is done by beam current measurement.

2) With a Neutral Beam, any material may be processed, including highly insulating materials and other materials that may be damaged by electrical charging effects, without the necessity of providing a source of target neutralizing electrons to prevent workpiece charging due to charge transported to the workpiece by an ionized beam. When employed with conventional GCIB, target neutralization to reduce charging is seldom perfect, and the neutralizing electron source itself often introduces problems such as workpiece heating, contamination from evaporation or sputtering in the electron source, etc. Since a Neutral Beam does not transport charge to the workpiece, such problems are reduced.

3) There is no necessity for an additional device such as a large aperture high strength magnet to separate energetic monomer ions from the Neutral Beam. In the case of conventional GCIB the risk of energetic monomer ions (and other small cluster ions) being transported to the workpiece, where they penetrate producing deep damage, is significant and an expensive magnetic filter is routinely required to separate such particles from the beam. In the case of the Neutral Beam apparatus of the invention, the separation of all ions from the beam to produce the Neutral Beam inherently removes all monomer ions.

One embodiment of the present invention provides a method of improving bioactivity of a surface of an implantable object, the method comprising: forming an accelerated Neutral Beam in a reduced-pressure chamber; introducing an object into the reduced-pressure chamber; wherein said object is selected from the group consisting of a medical prosthesis, a surgical implant, a component of a medical prosthesis, a component of a surgical implant, and other objects intended for implantation in a living mammal and further wherein at least a portion of the surface of the implantable object comprises a material selected from the group consisting of titania, titanium, an alloy of titanium, and polytetrafluoroethylene (PTFE); and irradiating at least a first portion of the surface of said object with the accelerated Neutral Beam.

The forming step may comprise: forming a gas-cluster ion-beam comprising ionized gas-clusters in a reduced-pressure chamber; accelerating the gas-cluster ion-beam; at least partially neutralizing the gas-cluster ion-beam to; and separating the at least partially neutralized gas-cluster ion-beam into a neutral portion and an ionized portion separate from the neutral portion to form the accelerated Neutral Beam. The separating step may comprise use of electrostatic separating means. The method may comprise at least partially dissociating the gas-cluster ion-beam. The Neutral Beam may be essentially free of intermediate size clusters. The Neutral Beam may be essentially a neutral monomer beam. The Neutral Beam may comprise neutral gas clusters.

Another embodiment of the present invention provides a method of inducing cell growth on or adjacent to an object, the method comprising: selecting at least a portion of a surface of an object, wherein said portion comprises a material selected from the group consisting of titania, titanium, an alloy of titanium, and polytetrafluoroethylene (PTFE); forming an accelerated Neutral Beam in a reduced-pressure chamber; introducing said object into said reduced-pressure chamber before or after pressure reduction therein; irradiating said at least a portion of said surface with said accelerated Neutral Beam; removing said object from said reduced-pressure chamber; and exposing said at least a portion of said surface to living cells.

Yet another embodiment of the present invention provides as article having a surface region comprising a material selected from the group consisting of titania, titanium, an alloy of titanium, and polytetrafluoroethylene (PTFE) with attached cells made by a method comprising the steps of: selecting at least a portion of a surface comprising polyether ether ketone of an object for attaching cells; forming an accelerated Neutral Beam in a reduced-pressure chamber; introducing said article into said reduced-pressure chamber before or after pressure reduction therein; irradiating said at least a portion of said surface with the accelerated Neutral Beam; removing said object from said reduced-pressure chamber; and exposing said at least a portion of said surface to living cells.

BRIEF DESCRIPTION OF THE DRAWINGS

For a better understanding of the present invention, together with other and further objects thereof, reference is made to the accompanying drawings, wherein:

FIGS. 7a and 7b are electron micrographs of portions of surfaces of PTFE substrates, wherein FIG. 7a shows a non-ion-beam-irradiated control portion and FIG. 7b shows an GCIB irradiated portion and wherein the GCIB irradiated portion shows significantly improved cellular attachment and/or proliferation in comparison to the control portion;

DETAILED DESCRIPTION OF THE PREFERRED METHODS AND EXEMPLARY EMBODIMENTS

Several exemplary embodiments are disclosed to show the wide scope and variety of material surfaces that can enjoy benefit of the GCIB or Neutral Beam processing method of the invention to enhance their bioactivity. These examples are chosen to illustrate that the application of the invention is broad and not limited to one or a few materials, but can be broadly exploited for a wide range of material surfaces.

Titanium Exemplary Embodiment

A titanium surface improvement is disclosed in an exemplary embodiment. Titanium is a material often employed in medical objects intended for implantation into a mammal. Titanium foil samples of 0.01 mm thickness were first cleaned in 70% isopropanol for 2 hours and then air dried in a bio-safety cabinet overnight. It is understood that the cleaned titanium foil samples, as with any titanium that has been exposed to normal atmospheric conditions, likely has a very thin native titania surface coating, which may be incomplete and may be imperfect. The foil samples were then either GCIB irradiated to a dose of $5\times10^{14}$ ions/cm$^2$ using an argon GCIB accelerated using 30 kV acceleration voltage or were left un-irradiated, as controls. The titanium foils (both the irradiated sample and control sample) were then cut into 0.9 cm×0.9 cm squares and placed at the bottom of individual wells (8 control squares and 8 GCIB irradiated squares) of a 24-well Multiwell™ polystyrene plate (BD Falcon 351147). Human fetal osteoblastic cells derived from bone (hFOB 1.19, ATCC CRL-11372) were sub-cultured and approximately 3500 cells were placed on top of each titanium foil square in 1 ml of (Invitrogen Corp.) Dulbecco's Modified Eagle Medium nutrient mixture F-12 (DMEM/F12) supplemented with 10% fetal bovine serum (FBS) and 0.3 mg/ml G418 antibiotic (also known as Geneticin) and incubated in a humidified incubator at 37° C. and 5% CO$_2$ in air. Following one day and five days of incubation, media samples were removed and cells were assayed using CellTiter 96® AQueous Cell Proliferation Assay from Promega used according to the manufacturer's instructions, with the measurement made using a Dynex OpsysMR plate reader at 490 nm wavelength. Assay solution was then removed from the wells and the titanium foils and the cells were then fixed by placing—20° C. chilled methanol on the titanium foil squares in the wells for at least 30 minutes. Following fixation, the titanium foil squares were then air-dried and osteoblast cells adhering to the titanium foil squares were imaged using a Hitachi TM1000 scanning electron microscope. Results showed that osteoblast cells adhered to the foils following one day of incubation were 694.5 cells±164.8 cells on the control foils and were enhanced to 2082.3 cells±609.2 cells on GCIB irradiated foils (P<0.03). The osteoblast cells proliferated and after five days incubation were 1598.7 cells±728.4 cells on controls as compared to 3898.0 cells±940.9 cells on GCIB irradiated foils (P<0.003).

Figure 1:
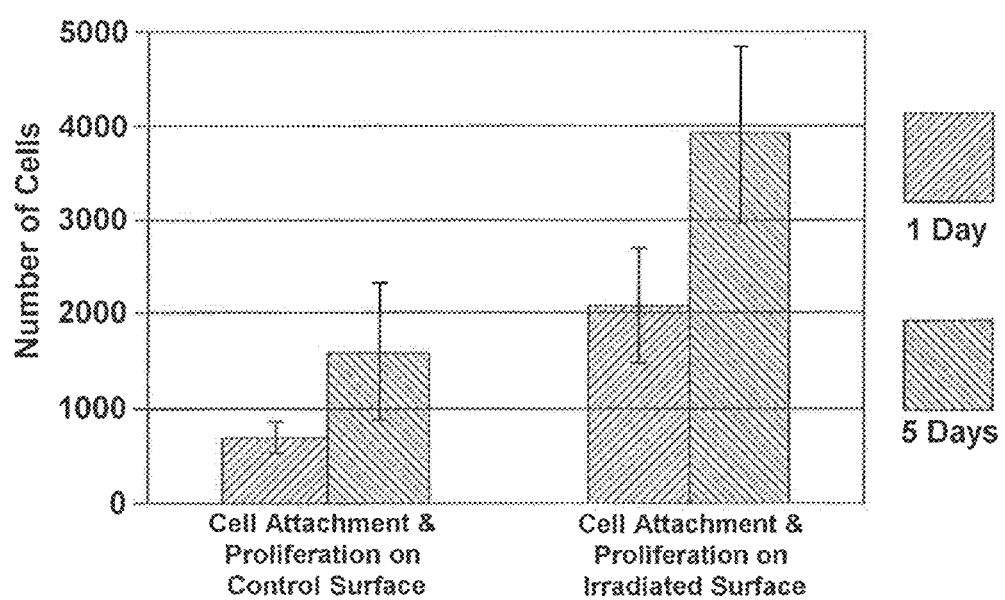
FIG. 1 is a chart comparing rates of cellular attachment and proliferation

FIG. 1 is a chart that shows that hFOB 1.19 human fetal osteoblastic cells attach to and proliferate at an enhanced rate on GCIB irradiated titanium foils as compared to control titanium foils.

Figure 2:
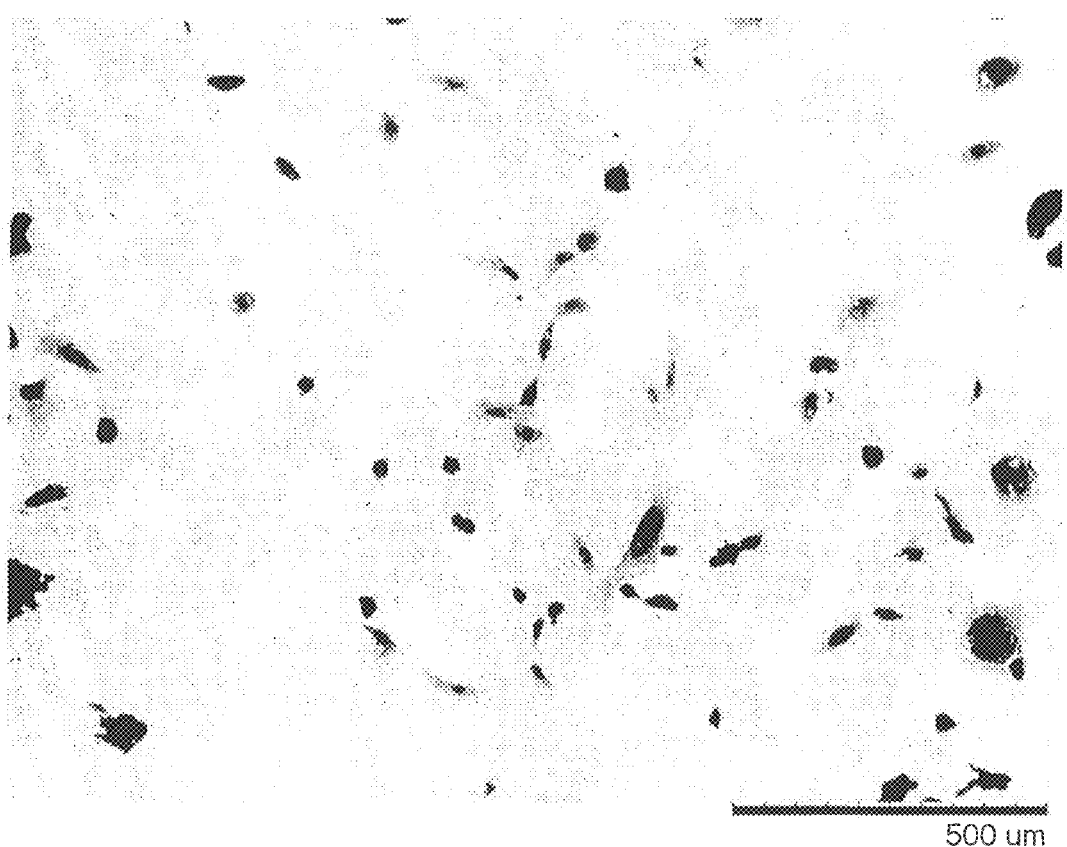
FIG. 2 is a scanning electron micrograph of a portion of a surface of an untreated titanium foil showing attachment of cells to the surface.
Figure 3:
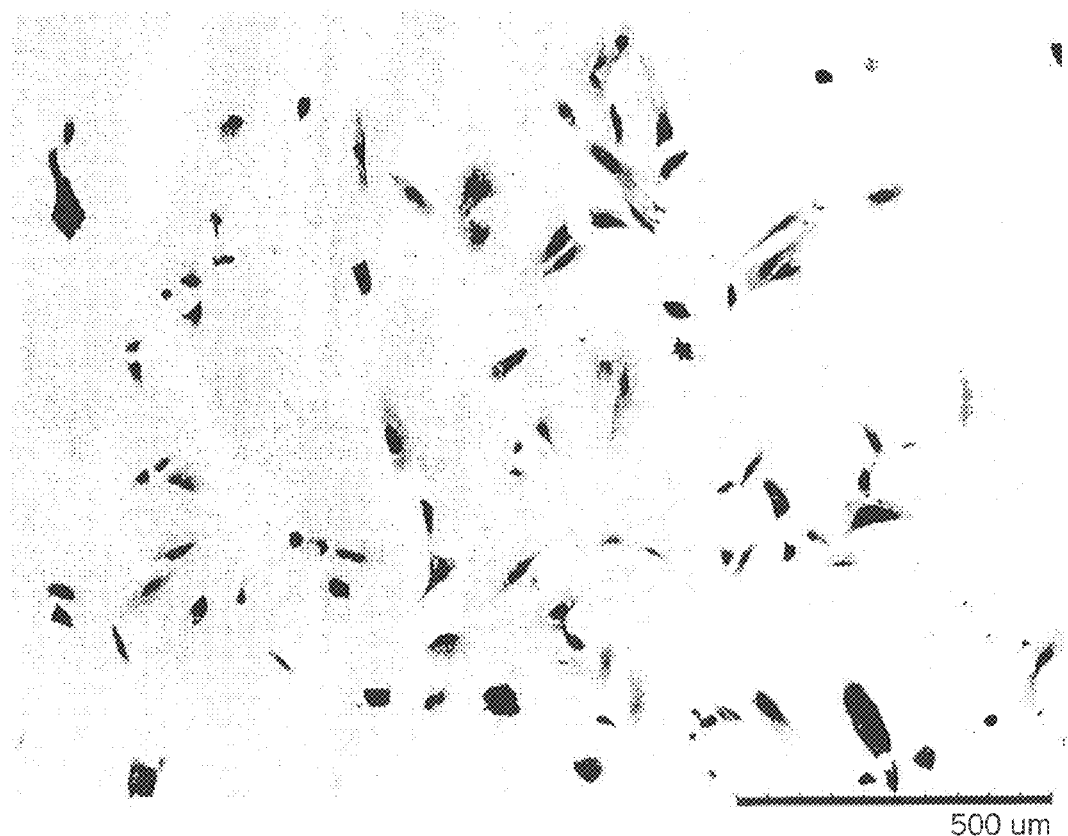
FIG. 3 is a scanning electron micrograph of a portion of a surface of a titanium foil processed by GCIB irradiation according to an embodiment of the invention showing improved attachment/proliferation of cells to the surface.

FIG. 2 is a scanning electron micrograph of a control titanium foil following 5 days incubation. FIG. 3 is a scanning electron micrograph of a GCIB irradiated titanium foil following 5 days incubation. Both FIG. 2 and FIG. 3 are shown at the same magnification and image equal surface areas. Comparison of FIG. 2 and FIG. 3 shows that the GCIB irradiated titanium foil (FIG. 3) has an increased degree of osteoblast cell attachment and that more osteoblast cells appear to be spreading and making cell-to-cell contact, which is known to be an important factor in initiating cell proliferation amongst anchorage-dependent cells such as osteoblasts and fibroblasts. GCIB irradiation of materials (such as titanium) employed in forming objects for medical/surgical implantation into a body of a mammal results in modification of the surface to make it more conducive to cell attachment and proliferation.

Employing this effect for improving the integration of a medical object intended for implant into a body or bodily tissue or onto a body of a mammal by making a surface of the object more conducive to cell attachment and proliferation involves the steps of 1) identifying an object for implant wherein it is desired to provide enhanced integration; 2) determining if all surfaces of the object require such enhancement or if it is preferable to limit the enhancement to only a portion of the surfaces of the object (as for example, a hip joint prosthesis wherein the portions that attach to bone benefit from improved attachment while the sliding portion of the ball or acetabular cup do not benefit from increased cellular attachment); and 3) GCIB irradiating only the portions of the surface of the medical object where enhanced integration is desired, and finally medically/surgically implanting the object (modified for enhanced integration) into the body of a mammal. Of course, if it is preferable that all portions of the surface of the medical object benefit from enhanced integration, then all portions of the surface are preferably GCIB irradiated.

Optionally, following the irradiation step and preceding the implanting step, integration may be further enhanced by including a step of growing and attaching (in vitro) cells onto the surface of the medical object. This may include isolating, culturing and in vitro attachment of cells from the particular individual in which the medical object is intended to be implanted, or it may include using cells obtained from another individual, or from stem cells or other pluripotent cells (from either the same or a differing species of mammal).

The irradiating step may optionally include the use of a mask or directed beam or other method for limiting GCIB processing to a selected portion of the object.

In the prior art, micro-roughened titanium surfaces have been shown to be preferential to osteoblast cell attachment. SLA titanium has been a commonly employed material for bone implants. The SLA process both improves the hydrophilicity and micro-roughens the surface. SLA titanium and control (smooth machined) titanium samples were compared, both with and without GCIB irradiation.

Titanium samples (1 cm×1 cm×0.6 mm), with both smooth-machined and SLA surfaces were compared, both with and without argon GCIB irradiation. The smooth-machined and SLA surfaces were characterized for roughness by atomic force microscope measurement techniques. Evaluated over 1-micrometer square scan areas, the average roughness (Ra) values of the two types of surfaces are shown in Table 1.

TABLE 1

| Titanium Sample | Ra (nm) |
| --- | --- |
| Smooth-Machined | 8.38 |
| SLA surface | 20.08 |

The smooth-machined and SLA surfaces were either irradiated with GCIB at a dose of $5\times10^{14}$ argon clusters/cm$^2$ at 30 kV acceleration voltage, or left un-irradiated as controls. The titanium pieces (9 samples for each condition, a total of 36 samples) were placed in individual wells in 24 well dishes and approximately 2500 primary human osteoblast cells were placed on each titanium sample in 1 ml of (Invitrogen Corp.) Dulbecco's Modified Eagle Medium nutrient mixture (DMEM) supplemented with 10% fetal bovine serum (FBS) and 1% penicillin/streptomycin and incubated in a humidified incubator at 37° C. and 5% $CO_2$ in air. Following three days, seven days, and ten days of incubation, three samples for each condition were removed from the media and cells were assayed using CellTiter 96® Aqueous Cell Proliferation Assay from Promega used according to the manufacturer's instructions, with the measurement made using a Dynex OpsysMR plate reader at 490 nm wavelength to assess cell attachment to the samples. Results are shown in Table 2.

TABLE 2

| | Cells Attached (average of three samples) | | |
| --- | --- | --- | --- |
| Sample Type | 3 Days | 7 Days | 10 Days |
| Smooth-Machined, Un-irradiated | 2400 | 7633 | 7567 |
| Smooth-Machined, GCIB irradiated | 3767 | 13600 | 17967 |
| SLA, Un-irradiated | 3800 | 7333 | 8100 |
| SLA, GCIB irradiated | 2767 | 7467 | 11700 |

The results shown in Table 2 show that little difference existed in cell proliferation between the un-irradiated smooth-machined and un-irradiated SLA titanium surfaces. On the other hand, it is seen that in both cases (smooth-machined and SLA surfaces) the proliferation was substantially enhanced on the GCIB irradiated surfaces. Furthermore, the improvement in proliferation was significantly greater on the smooth-machined (Ra=8.38 nm) surface as compared to the SLA (Ra=20.08 nm) surfaces. It is apparent that though micro-roughness from the SLA process has been considered a preferred surface condition for cell attachment and proliferation in the past, the GCIB irradiation provides superior results even at low roughness values (Ra<10 nm).

Glass Exemplary Embodiment

A glass surface improvement is disclosed in another exemplary embodiment. Glass is a material often employed in biological laboratory wares. Glass and glassy or glass-like materials are also employed in fabricating medical objects intended for implantation into a mammal. Thin glass substrates in the form of glass cover slips (Corning Glass 2865-25) were first cleaned in 70% isopropanol for 2 hours and then air-dried. The glass samples were then either GCIB irradiated to a dose of $5\times10^{14}$ ions/cm using an argon GCIB accelerated using 30 kV acceleration voltage or were left un-irradiated, as controls. The glass cover slips (both the irradiated sample and control sample) were then seeded with primary human osteoblast cells at an initial density of 40,000 cells per cm$^2$ in Dulbecco's Modified Eagle Medium nutrient mixture (DMEM) supplemented with 10% fetal bovine serum (FBS) and 1% penicillin/streptomycin and incubated in a humidified incubator at 37° C. and 5% $CO_2$ in air. The glass cover slips were viewed and imaged (optical microscopy) hourly for the first 4 hours to observe cellular attachment. After 4 hours, the nutrient mixture and non-adhering cells were then removed and replaced with fresh, supplemented, nutrient mixture and incubation was continued. Additional microscopic images were taken at 24 hours and 48 hours after seeding.

Figure 4A:
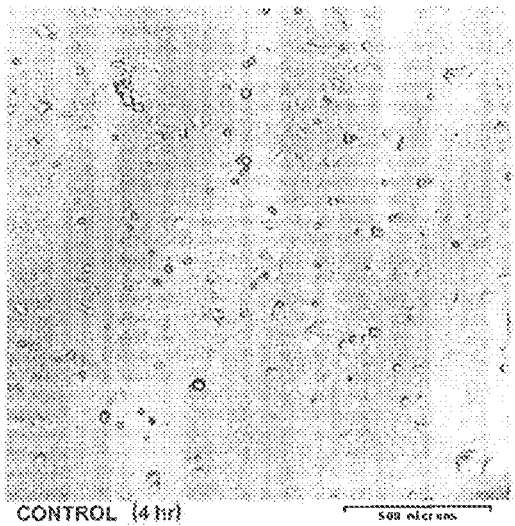
FIGS. 4a through 4f are optical micrographs of portions of surfaces of glass substrates, both controls and GCIB irradiated, according to an embodiment of the invention and showing improved attachment/proliferation of cells on the surface following GCIB irradiation.
Figure 4B:
Figure 4C:
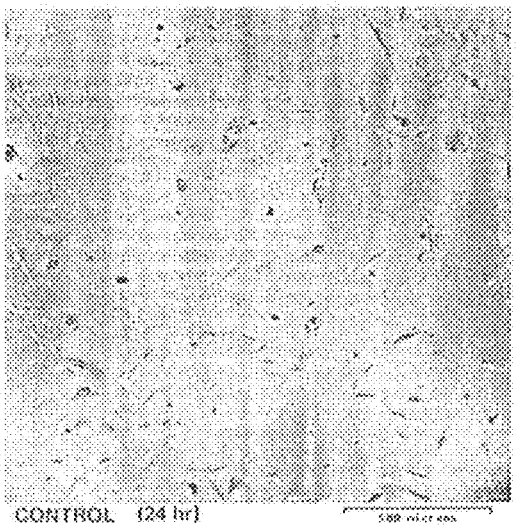
Figure 4D:
Figure 4E:
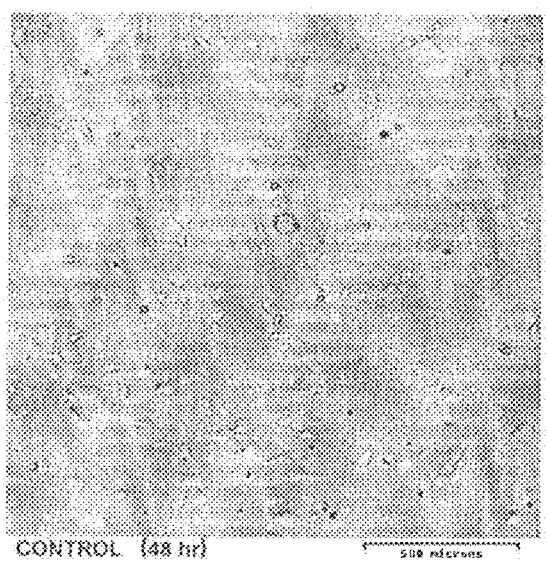
Figure 4F:
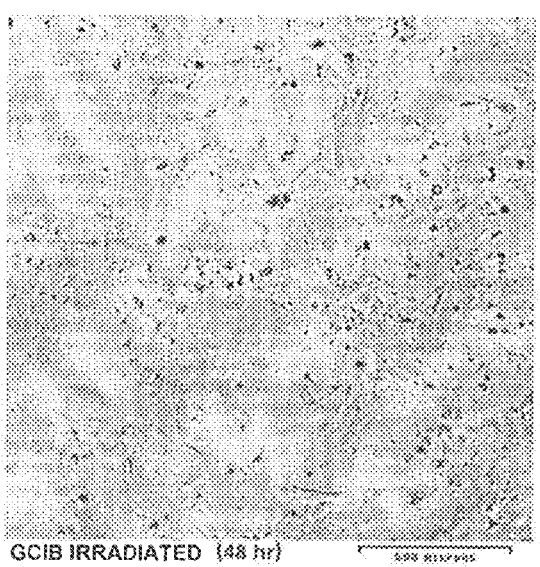

FIGS. 4a, 4c, and 4e are optical micrographs of the control glass cover slip taken at intervals of 4 hours, 24 hours, and 48 hours (respectively) after seeding with cells. FIGS. 4b, 4d, and 4f are optical micrographs of the GCIB irradiated glass covet slip also taken at intervals of 4 hours, 24 hours, and 48 hours (respectively) after seeding with cells. By comparing the controls with the GCIB irradiated surfaces at each time point, it is clear that the human fetal osteoblastic cells attach in greater numbers and proliferate better on the GCIB irradiated glass cover slip surface, compared to the un-irradiated controls.

Polymer Exemplary Embodiments

A first polymer surface improvement is disclosed in another exemplary embodiment. Polymer material is a material often employed in biological laboratory wares, for example polystyrene, polypropylene, etc. Polymer materials are also employed in fabricating medical objects intended for implantation into a mammal. Polystyrene substrates in the form of Petri dishes (Fisher Scientific Fisherbrand 08-757-12) were either GCIB irradiated to a dose of $5\times10^{14}$ ions/cm$^2$ using an argon GCIB accelerated using 30 kV acceleration voltage or were left un-irradiated, as controls. Additionally, a polystyrene substrate in the form of a cell culture dish (BD Biosiences 353003) was employed as an alternative polystyrene surface, for comparison. The cell culture dishes are commercially supplied with a specially treated surface intended to enhance cell growth. The three polystyrene samples (both the irradiated Petri dish sample and control Petri dish sample, as well as the un-irradiated alternative cell culture dish) were then seeded with primary human osteoblast cells at an initial density of 2,500 cells per cm$^2$ in Dulbecco's Modified Eagle Medium nutrient mixture (DMEM) supplemented with 10% fetal bovine serum (FBS)

and 1% penicillin/streptomycin and incubated in a humidified incubator at 37° C. and 5% $CO_2$ in air. The three polystyrene samples were viewed and imaged (optical microscopy) hourly for the first 4 hours to observe cellular attachment. After 4 hours, the nutrient mixture and non-adhering cells were then removed and replaced with fresh, supplemented, nutrient mixture and incubation was continued. Additional microscopic images were taken at 24 hours and 48 hours after seeding.

Figure 5A:
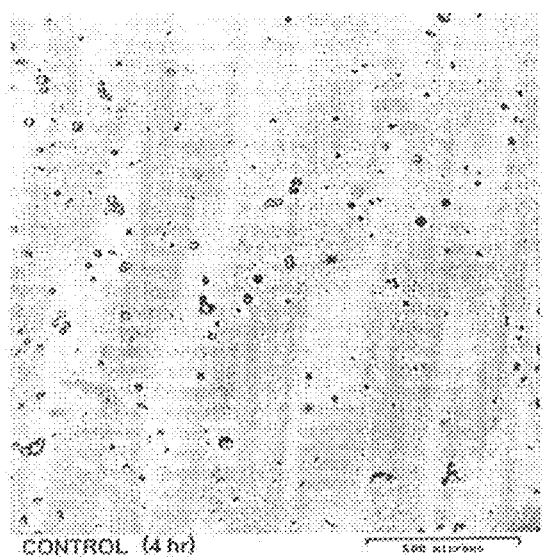
FIGS. 5a through 5i are optical micrographs of portions of surfaces of polystyrene substrates, including controls, GCIB irradiated, and commercial cell culture processed, according to an embodiment of the invention and showing improved attachment/proliferation of cells on the surface having received GCIB irradiation.
Figure 5B:
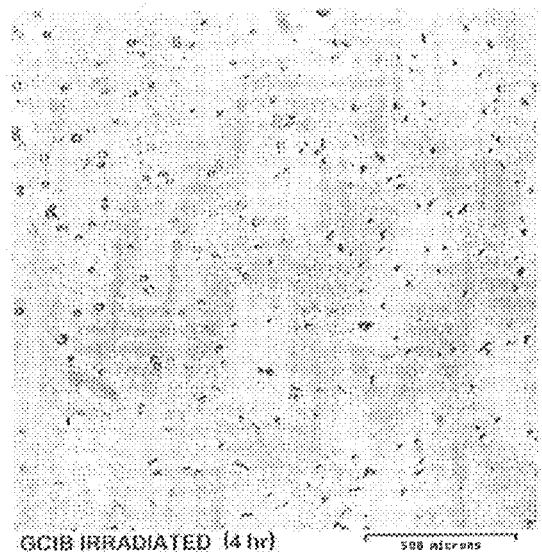
Figure 5C:
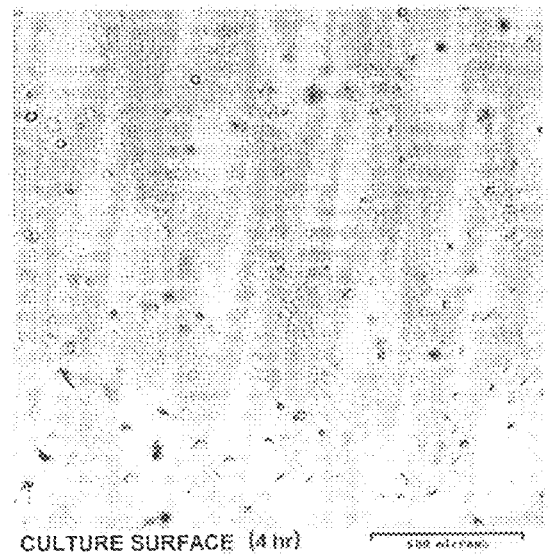
Figure 5D:
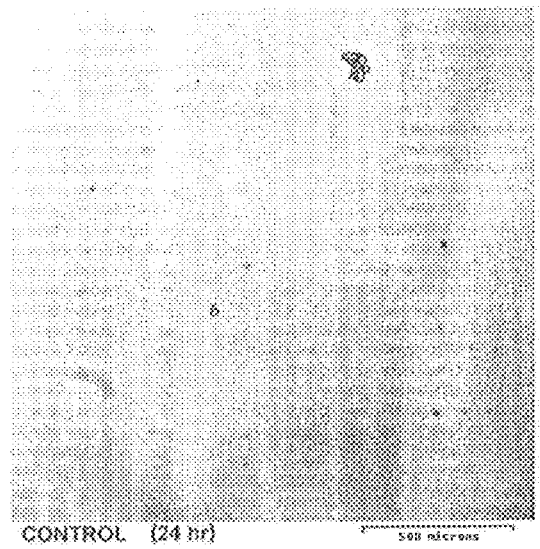
Figure 5E:
Figure 5F:
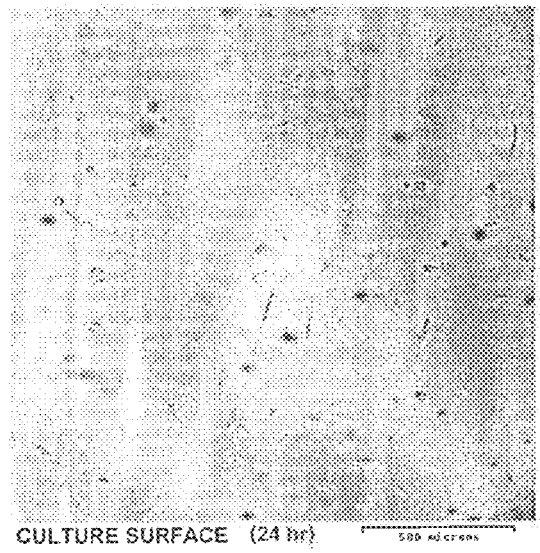
Figure 5G:
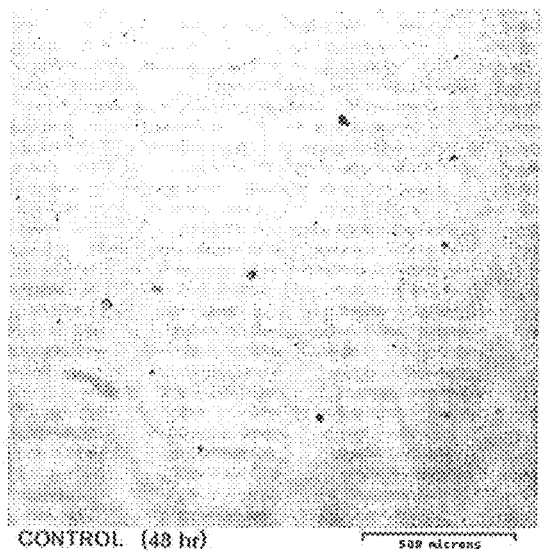
Figure 5H:
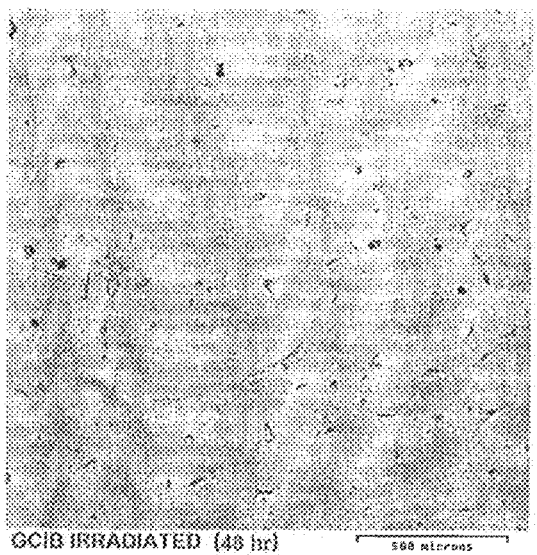
Figure 5I:
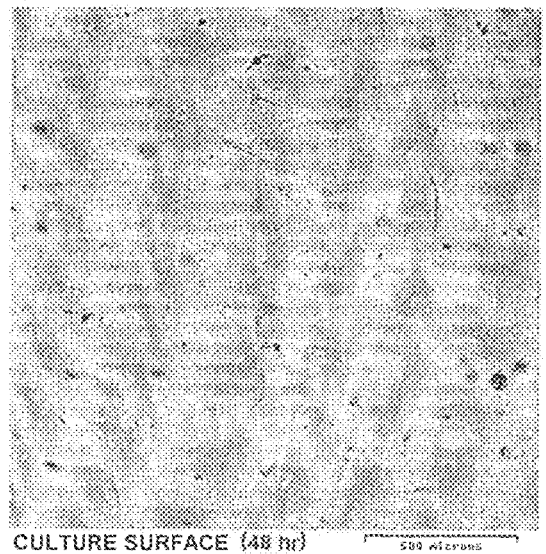

FIGS. 5a, 5d, and 5g are optical micrographs of the surface of the control polystyrene Petri dish taken at intervals of 4 hours, 24 hours, and 48 hours (respectively) after seeding with cells. FIGS. 5b, 5e, and 5h are optical micrographs of the GCIB irradiated polystyrene Petri dish also taken at intervals of 4 hours, 24 hours, and 48 hours (respectively) after seeding with cells. FIGS. 5c, 5f, and 5i are optical micrographs of the GCIB irradiated polystyrene cell culture dish, again taken at intervals of 4 hours, 24 hours, and 48 hours (respectively) after seeding with cells. By comparing the Petri dish control with the GCIB irradiated Petri dish surface and the surface of the un-irradiated cell culture dish at each time point, it is clear that the human fetal osteoblastic cells attach in greater numbers and proliferate better on the GCIB irradiated glass cover slip surface, compared to either the un-irradiated Petri dish control or the un-irradiated cell culture dish surface.

A further polystyrene substrate in the form of a Petri dish (Fisher Scientific Fisherbrand 08-757-12) was partially masked and then GCIB irradiated to a dose of $5 \times 10^{14}$ ions/cm$^2$ using an argon GCIB accelerated using 30 kV acceleration voltage. The mask employed was a non-contact shadow mask in proximity to the polystyrene surface. The unmasked portion received the full GCIB dose, while the masked portion received no GCIB irradiation, thus serving as a control surface. The Petri dish was then seeded with primary human osteoblast cells at an initial density of 2,500 cells per cm$^2$ in Dulbecco's Modified Eagle Medium nutrient mixture (DMEM) supplemented with 10% fetal bovine serum (FBS) and 1% penicillin/streptomycin and incubated in a humidified incubator at 37° C. and 5% $CO_2$ in air. The polystyrene Petri dish was viewed (optical microscopy at the interface between the GCIB irradiated and un-irradiated regions) hourly for the first 4 hours to observe cellular attachment. After 4 hours, the nutrient mixture and non-adhering cells were then removed and replaced with fresh, supplemented, nutrient mixture and incubation was continued. Microscopic images were taken at 24 hours and 48 hours after seeding.

Figure 6A:
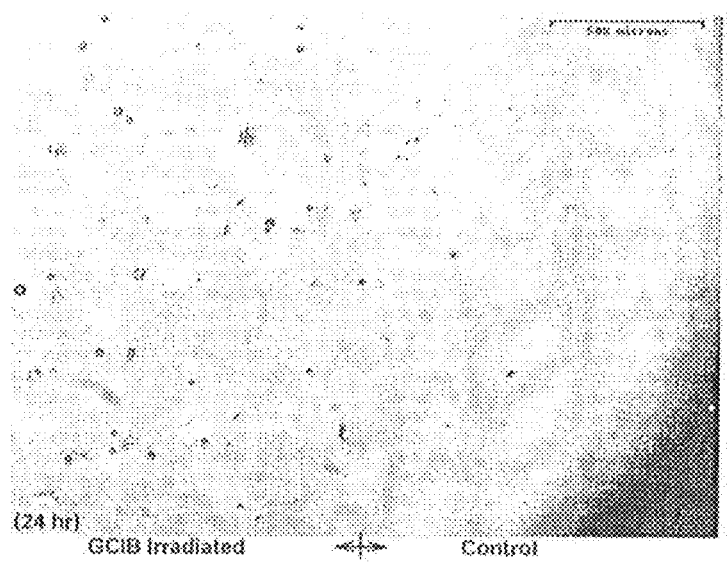
FIGS. 6a and 6b are optical micrographs of portions of a surface of a polystyrene substrate, wherein a portion of the surface was masked during GCIB irradiation, so as to show side-by-side comparison of the un-irradiated masked portion with the GCIB irradiated portion and showing improved attachment/proliferation of cells on the GCIB irradiated portion.
Figure 6B:
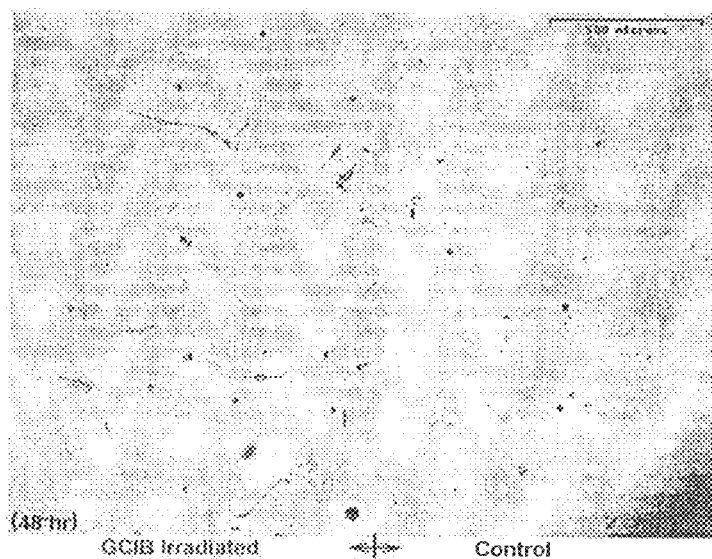

FIGS. 6a, and 6b are optical micrographs of the partially masked polystyrene Petri dish taken at intervals of 24 hours, and 48 hours (respectively) after seeding with cells and viewed at the interface between the masked un-irradiated and the unmasked GCIB irradiated regions. The GCIB irradiated region is on the left side of each of FIGS. 6a and 6b and the un-irradiated control region is on the right side of each of FIGS. 6a and 6b. By comparing the un-irradiated and the GCIB irradiated regions at both time points, it is clear that the human fetal osteoblastic cells attach in greater numbers and proliferate better on the GCIB irradiated portion of the polystyrene surface, compared to the un-irradiated (masked) portion.

A second polymer surface improvement is disclosed in another exemplary embodiment. Polytetrafluoroethylene (PTFE) substrates in the form of strips (30 mm long×10 mm wide×1.5 mm thick) were masked on one half and GCIB irradiated to a dose of $5 \times 10^{14}$ ion/cm$^2$ using an argon GCIB accelerated using 30 kV acceleration voltage or were left un-irradiated, as controls. The mask employed was a non-contact shadow mask in proximity to the PTFE surface. The unmasked surface portions received the full GCIB dose, while the masked surface portions received no GCIB irradiation, thus serving as a control surface. Primary porcine fibroblast cells were harvested from fresh anterior ligament. The entire (irradiated and control portions) PTFE surfaces were seeded at an initial density of 5000 cells per cm$^2$ with the primary porcine fibroblast cells and allowed to attach for 24 hours in Dulbecco's Modified Eagle Medium nutrient mixture (DMEM) supplemented with 10% fetal bovine serum (FBS) and 1% penicillin/streptomycin and incubated in a humidified incubator at 37° C. Following 24 hours, media was removed and cells were briefly rinsed with 1× phosphate buffered saline and fixed in methanol pre-chilled at −20 degrees C. for 1 hour. Surfaces of the PTFE at the GCIB-irradiated portion, and at the non-GCIB-irradiated control portion were each imaged using a Hitachi TM-1000 scanning electron microscope. Results showed that there is a clear distinction between the cell attachment on the GCIB-irradiated portion versus the non-GCIB-irradiated portion of the PTFE surface.

Figure 7A:
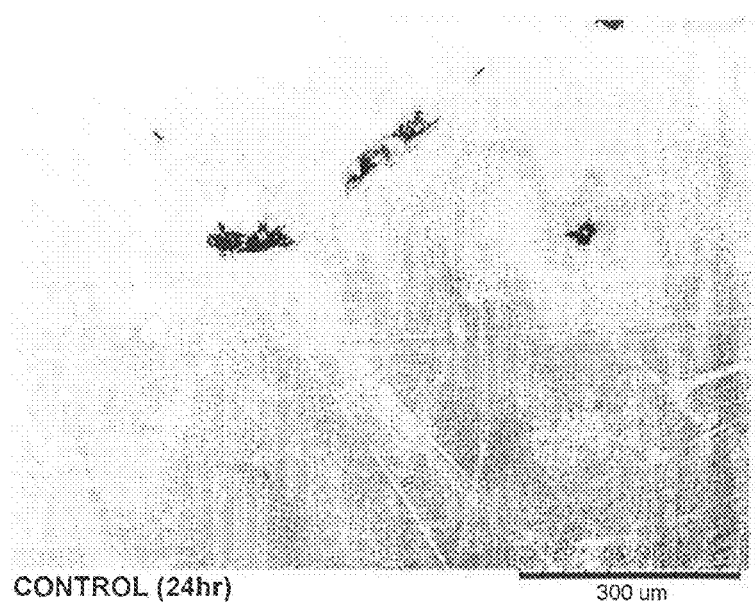
Figure 7B:
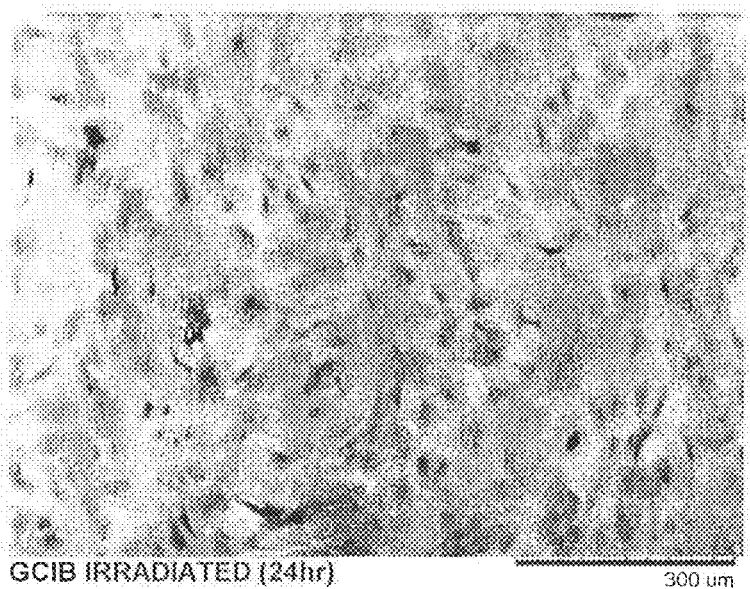

FIG. 7a is a scanning electron micrograph of the non-GCIB-irradiated control surface of the PTFE substrate taken 24 hours after seeding with cells. FIG. 7b is a scanning electron micrograph of the GCIB-irradiated surface of the PTFE substrate also taken 24 hours after seeding with cells (both following fixation).

FIG. 7a shows that cells attached to less than 1% of the non-GCIB-irradiated control portion of the PTFE surface.

FIG. 7b shows that cells attached to nearly 100% of the GCIB-irradiated portion of the PTFE surface.

This ability to impact cell attachment on a surface can be extremely useful in many applications where cell growth is desired in only restricted areas. Examples include cardiovascular stents that can be GCIB-irradiated on the luminal surface allowing re-endothelialization and maintaining intact (un-irradiated) surface on the abluminal surface to suppress smooth muscle growth and plaque formation. Such stents can be fabricated from PTFE, cobalt-chrome alloy, or other materials. Optionally, the abluminal surfaces of such stents may be drug coated using known technologies to inhibit the growth of smooth muscle (and/or other cells) on the abluminal surface, thus reducing risk of restenosis. Other example applications include GCIB-irradiation of silicone rubber tubes to allow nerve regeneration, and other such.

A third polymer surface improvement is disclosed in another exemplary embodiment. Polyether ether ketone (PEEK) is becoming a favored replacement for titanium in many surgical implant applications. PEEK provides a greater degree of flexibility than titanium, which is desirable in many applications (as for example fabrication of spinal fusion cages). PEEK may be employed in an essentially pure form, but has also been employed in carbon-fiber reinforced forms (and potentially in co-polymeric forms with other materials.) A disadvantage of PEEK is that it is that it is not as cyto-compatible or bioactive as some other materials (including titanium). Therefore, PEEK implants do not always integrate as well as desired.

The compatibility and bioactivity of PEEK are improved by GCIB-irradiation, making the material more suitable for surgical implant in situations where cell attachment and integration is desired. PEEK sheets of 0.005 inch thickness were pre-cleaned by placing them in 70% isopropyl alcohol for 2 hours, followed by 4 washes in double-distilled water for 15 minutes per wash, followed by 15 minutes under UV light in a biological hood. The PEEK sheets were then irradiated by argon GCIB to a dose of $5\times10^{14}$ argon gas cluster ions per cm$^2$ (or left unirradiated as controls), cut into ½ inch diameter circular disks, and then UV illuminated for an additional 15 minutes. The PEEK disks were placed in individual wells of 24-well sterilized polystyrene plates (non tissue culture treated to avoid having cells attach to the plastic of the plates). Human osteoblast cells were seeded onto the surface of the PEEK disks at a concentration of 3,000 cells/ml in Dulbecco's Modified Eagle Medium nutrient mixture (DMEM) supplemented with 10% fetal bovine serum (FBS) and 1% penicillin/streptomycin and incubated in a humidified incubator at 37° C. with 5% $CO_2$ in air. One ml of cell suspension was seeded per PEEK disk, with n=3 per condition (irradiated/not irradiated) and incubation time (4, 7, and 11 days). Cells were allowed to attach for 24 hours on all the PEEK disks and then the media and any unattached cells were aspirated and fresh media was replaced and plates returned to the incubator. Cells were subsequently allowed to attach and proliferate on the surface of the PEEK disks while incubated for up to 11 days. At each experimental time interval (4 days, 7 days, and 11 days post seeding), the PEEK samples were observed microscopically, verifying that essentially 100% cell attachment to the PEEK surface had occurred and each PEEK disk was removed from its well and media and placed in new wells that had not previously contained cells or media. Fresh media with MTS/PMS proliferation assay reagents per manufacturer's instructions (Promega, G5421) was used for cell assay and the cell assay was measured using a plate reader operating at a wavelength of 490 nm. Absorbance readings were converted to cell numbers based on a calibration curve previously generated with known cell numbers according to the MTS/PMS assay manufacturer's procedure to characterize the number of attached cells on each PEEK sample. Following each assay, the PEEK samples with attached cells were examined to confirm cell attachment and cell growth on the PEEK by scanning electron microscope examination and by DAPI fluorescent stain imaged by optical fluorescence microscopy.

Figure 8:
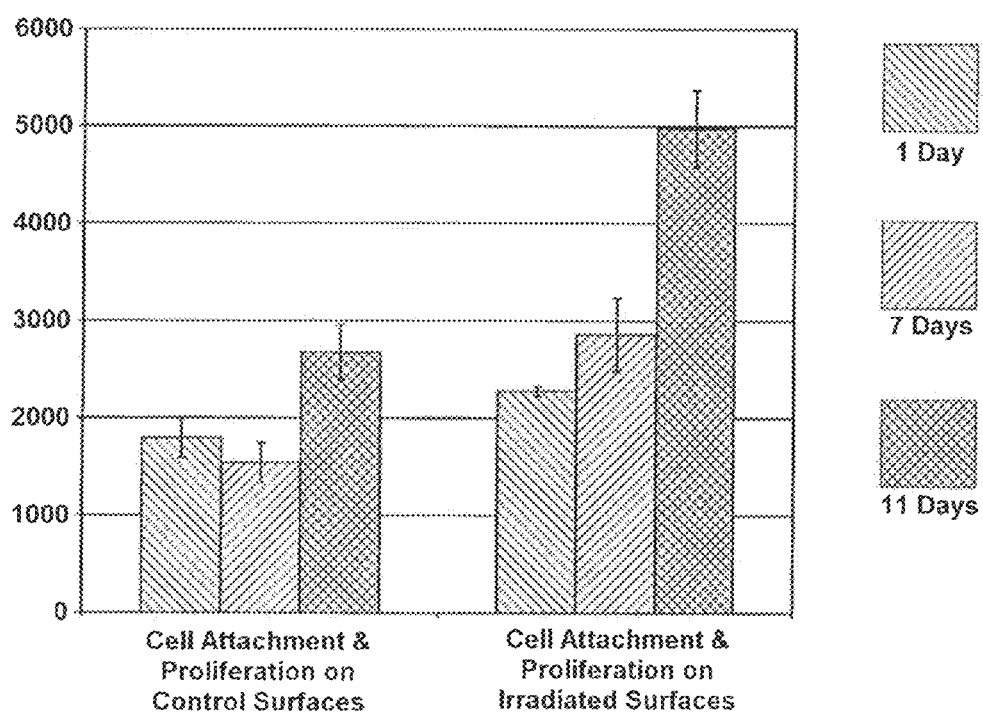
FIG. 8 is a chart comparing rates of cellular attachment and proliferation on unirradiated and GCIB irradiated PEEK substrates.

FIG. 8 is a chart summarizing the results of the PEEK proliferation and attachment experiment described above. The bars (with standard deviations indicated by error bars) show the MTS/PMS proliferation assay results for unirradiated control PEEK surfaces and GCIB irradiated PEEK surfaces at intervals of 1, 7, and 11 days after seeding. By day 11, a significant increase in cell proliferation is seen on the GCIB-irradiated PEEK (4,975±397 cells) as compared to controls (2,675±278 cells; p<0.028). This result indicates that GCIB-irradiation of PEEK surfaces results in enhanced cellular attachment and proliferation relative to un-GCIB-irradiated PEEK surfaces.

Amorphous Quartz Exemplary Embodiment

An amorphous quartz surface process is disclosed in another exemplary embodiment. Amorphous quartz material is a material often employed in biological laboratory wares, also employed in fabricating medical objects intended for implantation into a mammal. Amorphous quartz is known to be a very favorably material for surface attachment and proliferation of cells. A clean and sterile amorphous quartz substrate was partially masked and then GCIB irradiated to a dose of $5\times10^{14}$ ions/cm$^2$ using an argon GCIB accelerated using 30 kV acceleration voltage. The mask employed was a non-contact shadow mask in proximity to the quartz surface. The unmasked portion received the full GCIB dose, while the masked portion received no GCIB irradiation, thus serving as a control surface. Primary porcine fibroblast cells were harvested from fresh anterior ligament. The amorphous quartz surface was seeded at an initial density of 5,000 cells per cm$^2$ with the primary porcine fibroblast cells in Dulbecco's Modified Eagle Medium nutrient mixture (DMEM) supplemented with 10% fetal bovine serum (FBS) and 1% penicillin/streptomycin and incubated in a humidified incubator at 37° C. and 5% $CO_2$ in air. After 4 hours, the medium and non-adherent cells were then removed and replaced with fresh medium and incubation continued. The surface was viewed and imaged hourly for the first 4 hours and additionally at 6, 24, and 48 hours after initial seeding.

Figure 9:
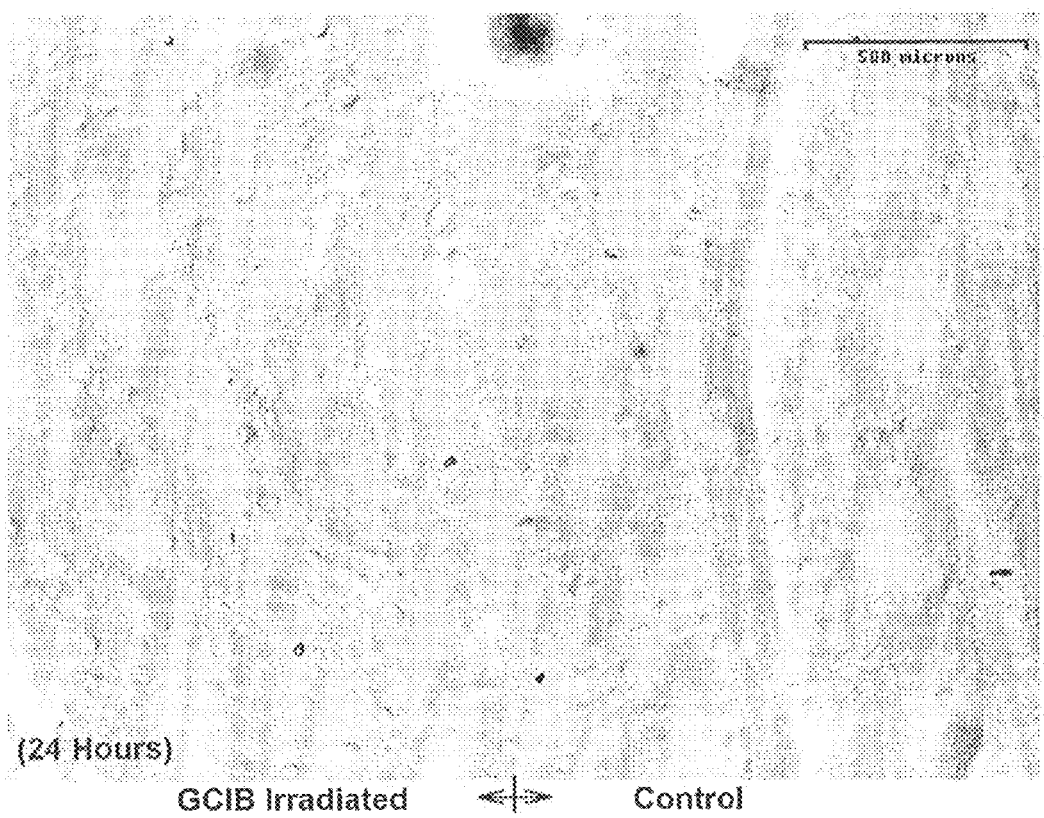
FIG. 9 is an optical micrograph of portions of a surface of an amorphous quartz substrate, wherein a portion of the surface was masked during GCIB irradiation, so as to show side-by-side comparison of the un-irradiated masked portion with the GCIB irradiated portion and showing a high degree of attachment/proliferation of cells on both the GCIB irradiated portion and the un-irradiated portions.

FIG. 9 is an optical micrograph of the partially masked amorphous quartz substrate taken at 24 hours after seeding with cells and viewed at the interface between the masked un-irradiated and the unmasked GCIB irradiated regions. The results show that fibroblast cells attach preferentially to the amorphous quartz surface on the GCIB irradiated sides to a moderate degree. The GCIB irradiated region is on the left side of FIG. 9 and the un-irradiated control region is on the right side of FIG. 9.

Crystalline Sapphire Exemplary Embodiment

A (single crystal) crystalline sapphire surface improvement is disclosed in another exemplary embodiment. A clean and sterile crystalline sapphire substrate was partially masked and then GCIB irradiated to a dose of $5\times10^{14}$ ions/cm$^2$ using an argon GCIB accelerated using 30 kV acceleration voltage. The mask employed was a non-contact shadow mask in proximity to the sapphire surface. The unmasked portion received the full GCIB dose, while the masked portion received no GCIB irradiation, thus serving as a control surface. Primary porcine fibroblast cells were harvested from fresh anterior ligament. The crystalline sapphire surface was seeded at an initial density of 5,000 cells per cm$^2$ with the primary porcine fibroblast cells in Dulbecco's Modified Eagle Medium nutrient mixture (DMEM) supplemented with 10% fetal bovine serum (FBS) and 1% penicillin/streptomycin and incubated in a humidified incubator at 37° C. and 5% $CO_2$ in air. After 4 hours, the medium and non-adherent cells were then removed and replaced with fresh medium and incubation continued. The surface was viewed and imaged hourly for the first 4 hours and additionally at 6, 24, and 48 hours after initial seeding.

Figure 10:
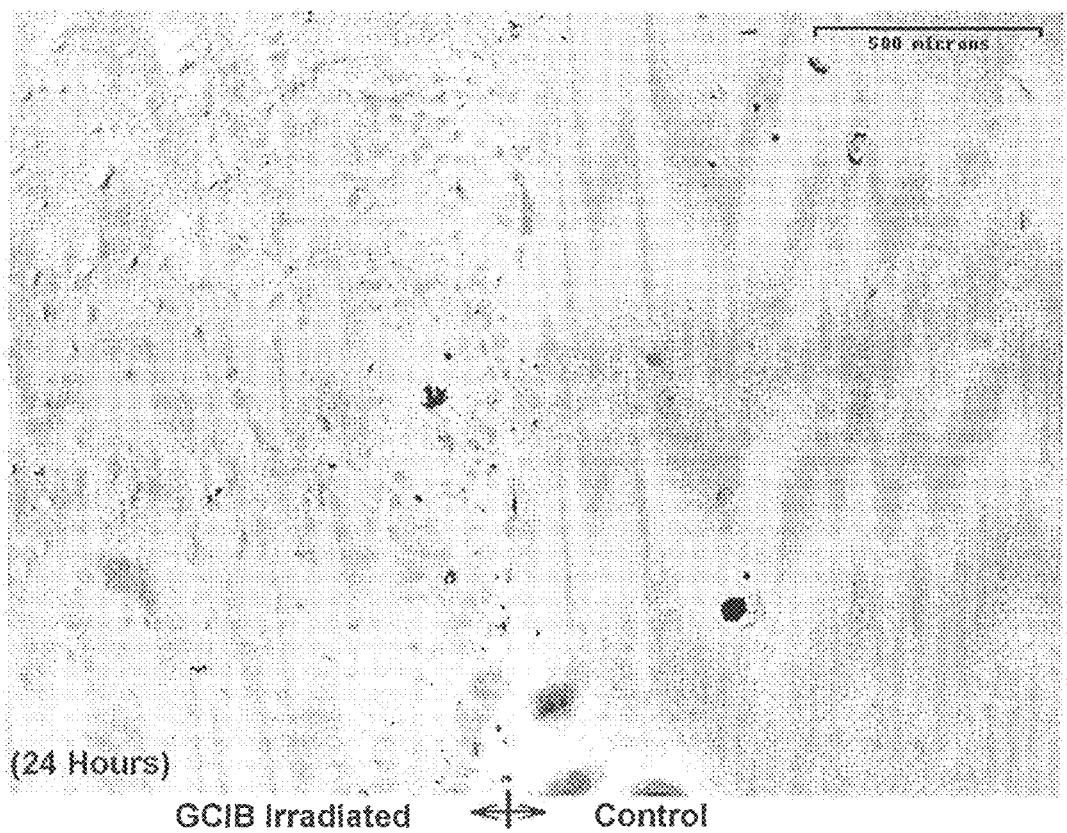
FIG. 10 is an optical micrograph of portions of a surface of a crystalline sapphire substrate, wherein a portion of the surface was masked during GCIB irradiation, so as to show side-by-side comparison of the un-irradiated masked portion with the GCIB irradiated portion and showing a high degree of attachment/proliferation of cells on the GCIB irradiated portion.

FIG. 10 is an optical micrograph of the partially masked crystalline sapphire substrate taken at 24 hours after seeding with cells and viewed at the interface between the masked un-irradiated and the unmasked GCIB irradiated regions. The GCIB irradiated region is on the left side of FIG. 10 and the un-irradiated control region is on the right side of FIG. 10. By comparing the un-irradiated and the GCIB irradiated regions, it is clear that the porcine fibroblast cells attach in greater numbers and proliferate better on the GCIB irradiated portion of the crystalline sapphire surface, compared to the un-irradiated (masked) portion.

It is believed that GCIB irradiation of a crystalline material like sapphire results in partial or complete amorphization of a very thin surface layer (a few tens of angstroms). Without wishing to be bound to any particular theory, it appears that the amorphizing surface modification effected by the irradiation contributes to the improved cellular attachment and proliferation. Other possible mechanisms that may contribute to the improvement are increasing the surface wettability, hydrophilicity and/or modification of the surface charge state of the material.

Polymer Filament/Polymer Fabric Exemplary Embodiments

Fibers, filaments, and fabrics can be formed from polymer or co-polymer fibers by weaving, knitting, braiding, and/or by other non-woven techniques. Certain polymer fabrics (most notably polyethylene terephthalate) are particularly suitable fabrics for making vascular grafts. Fabric of woven polyethylene terephthalate (sometimes written as poly(ethylene terephthalate) and abbreviated PET, or PETE) fibers may also be referred to by one of its tradenames, Dacron, and is commonly employed as a material for fabricating vascular grafts. In another exemplary embodiment, surface improvements are disclosed for a woven polyethylene terephthalate (PETE) fabric. Vascular grafts fabricated from PETE fabric are sometimes coated with a protein (such as collagen or albumin) to reduce blood loss and/or coated with antibiotics to prevent graft infection. Most strategies designed to reduce restenosis by the use of pharmacological or biological reagents involve direct inhibition of vascular smooth muscle cell proliferation on the fabric surface. However, as an alternative, smooth muscle cell proliferation may be indirectly inhibited by specific facilitation of re-endothelialization at injury and graft sites. In the past, re-endotheliaziation has often been slow or incomplete. In this embodiment we have evaluated GCIB irradiation of uncoated, woven PETE fabric material to show that it makes the material more bioactive and more suitable to facilitate re-endothelialization.

Woven PETE fabric was cut into 15 mm×30 mm pieces. The pieces were masked on one half and GCIB irradiated to a dose of $5 \times 10^{14}$ ions/cm$^2$ using an argon GCIB accelerated using 30 kV acceleration voltage. The mask employed was a non-contact shadow mask in proximity to the PETE fabric surfaces and covering half of one side of each of the fabric pieces. The unmasked surface portions received the full GCIB dose, while the masked surface portions received no GCIB irradiation, thus serving as a control surface. The fabric pieces were placed in individual Petri dishes and live mouse endothelial cells (EOMA cell line) were seeded onto the entire (irradiated and control portions) PETE fabric surface at an initial density of 50,000 cells per fabric piece and allowed to attach for 24 hours in Dulbecco's Modified Eagle Medium nutrient mixture (DMEM) supplemented with 10% fetal bovine serum (FBS) and 1% penicillin/streptomycin during incubation in a humidified incubator at 37° C. Following 24 hours, media and un-adhered cells were removed. Methanol, pre-chilled at −20 degrees C. for 1 hour, was placed on the PETE fabric for 10 minutes to fix adherent cells. The fabric and adhered mouse endothelial cells were then imaged by scanning electron microscope. Surface regions of both the GCIB irradiated and unirradiated control portions of the PETE fabric with attached mouse endothelial cells were imaged using a Hitachi TM-1000 scanning electron microscope. Results showed that there is a clear distinction between the cell attachment on the GCIB-irradiated portion versus the non-GCIB-irradiated portion of the PETE woven fabric surface.

Figure 11:
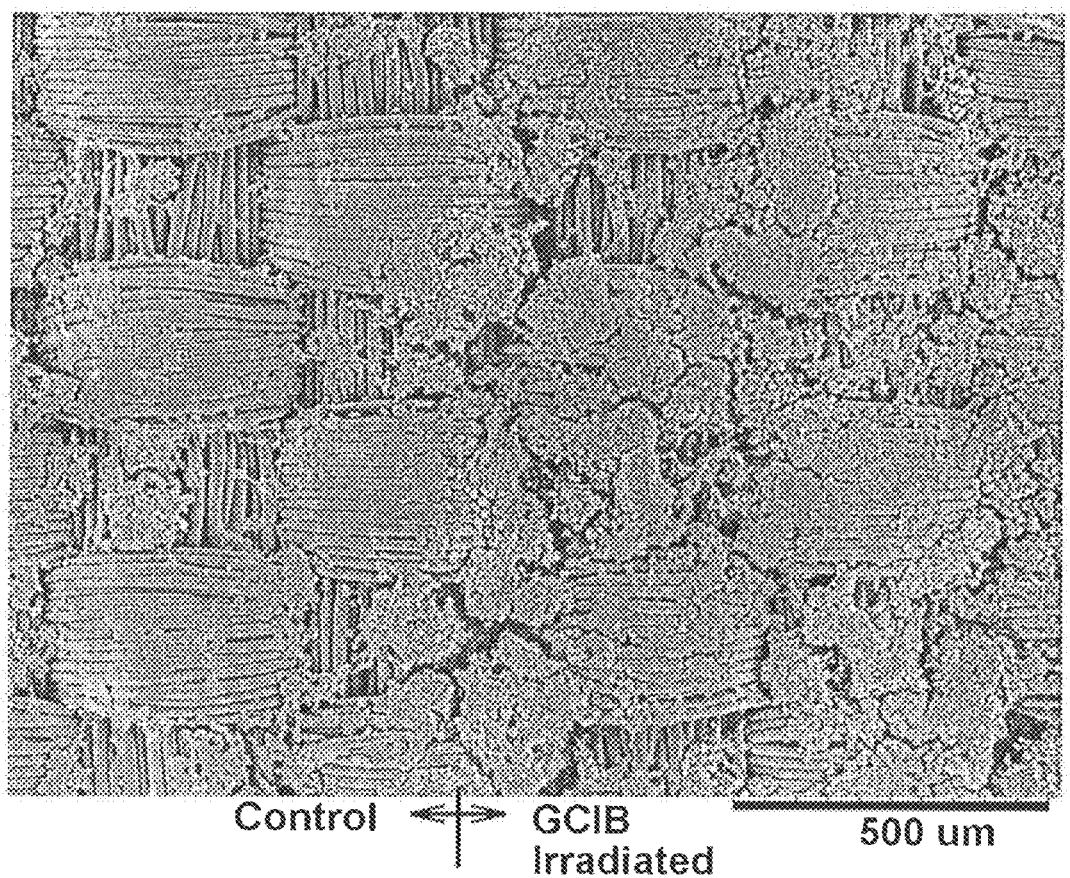
FIG. 11 is a scanning electron micrograph of portions of a surface of a PETE fabric surface, wherein a portion of the fabric surface was masked during GCIB irradiation so as to show side-by side comparison of the un-irradiated masked portion with the GCIB irradiated portion and showing preferential attachment of cells to the GCIB irradiated portion.

FIG. 11 is a scanning electron micrograph of a treated piece of PETE fabric surface made 24 hours after seeding with mouse endothelial cells (following methanol fixation). The portion of the PETE fabric on the left side of the image is the masked portion of the PETE fabric that was not irradiated prior to seeding. The portion of the PETE fabric on the right side of the image is the portion that received GCIB irradiation prior to seeding with cells.

FIG. 11 shows that re-endothelialization by mouse endothelial cells progressed significantly further on the GCIB irradiated portion of the PETE fabric than on the unirradiated control portion. EOMA cells preferentially adhered to the portion of PETE fabric that received GCIB irradiation.

Polymer or co-polymer fibers/filaments are often employed as surgical sutures. Surgical sutures may be monofilament or may be multistranded (twisted and/or braided) comprising multiple monofilaments. Certain polymer filaments (for example polyethylene and polyesters such as polyethylene terephthalate) are particularly suitable as braided sutures. Structures comprising multistranded polyethylene terephthalate (sometimes written as poly(ethylene terephthalate) and abbreviated PET, or PETE) fibers may also be referred to by one of its tradenames, Dacron, and are commonly employed as materials for non-absorbable sutures. In one commonly used commercially available type of non-absorbable suture, a braided composite of a polyester material (polyethylene terephthalate) is employed. In another commonly used commercially available type of non-absorbable suture, a multistranded long chain ultra-high molecular weight polyethylene (UHMWPE) core with a jacket of braided strands of (UHMWPE) and polyester is employed. For both these two types of commercially available sutures we have evaluated the application if GCIB irradiation to render the surfaces of the materials more bioactive and to provide for enhanced cell adhesion to and proliferation on the suture surface.

In a first evaluation of GCIB enhancement of suture material, Ethibond Excel (sourced by Ethicon Inc., Somerville N.J., USA) multistranded braided polyethylene terephthalate (PETE) sterile suture pieces of 2 cm length were either GCIB irradiated to a dose of $3.2 \times 10^{16}$ ions/cm$^2$ using an argon GCIB accelerated using 30 kV acceleration voltage or were left un-irradiated as controls, with n=3 per condition (irradiated/not irradiated). For cell seeding, the suture pieces (irradiated and controls) were placed in individual media troughs containing mesenchymal stem cells (MSC) at a concentration of 50,000 cells per suture piece and cells were allowed to attach for 24 hours. The suture pieces were then removed from the seeding media and placed in culture tubes with fresh media and incubated for 7 days. After 7 days post-seeding, cell counts were performed using a cell proliferation assay (Promega, MTS). The sutures displayed an average of 7667±630 attached cells for un-irradiated controls and 12429±3825 attached cells for GCIB irradiated samples ($p<0.03$).

In a second evaluation of GCIB enhancement of suture material, Ethibond Excel (sourced by Ethicon Inc., Somerville N.J., USA) multistranded braided polyethylene terephthalate (PETE) sterile suture pieces of 2 cm length were either GCIB irradiated to a dose of $6.7 \times 10^{16}$ ions/cm$^2$ using an argon GCIB accelerated using 30 kV acceleration voltage or were left un-irradiated as controls, with n=3 per condition (irradiated/not irradiated). For cell seeding, the suture pieces (irradiated and controls) were suspended in individual media troughs containing MC3T3/E1 mouse pre-osteoblast cells at a concentration of 150,000 cells per suture piece and cells were allowed to attach for 24 hours. The suture pieces were then removed from the seeding media and placed in culture tubes with fresh media and incubated for 7 days. After 7 days post-seeding, cell counts were performed using a cell proliferation assay (Promega, MTS). The sutures displayed an average of 27833±13950 attached cells for un-irradiated controls and 74190±7686 attached cells for GCIB irradiated samples ($p<0.0001$).

In a third evaluation of GCIB enhancement of suture material, Fiberwire (Arthrex, Inc., Naples, Fla., USA) sutures consisting of a multistranded long chain ultra-high molecular weight polyethylene (UHMWPE) core with a jacket of braided strands of (UHMWPE) and polyester was employed. Sterile suture pieces of 2 cm length were either GCIB irradiated to a dose of $6.7 \times 10^{16}$ ions/cm$^2$ using an argon GCIB accelerated using 30 kV acceleration voltage or were left un-irradiated as controls, with n=3 per condition (irradiated/not irradiated). The suture pieces (irradiated and controls) were suspended in individual media troughs containing MC3T3/E1 mouse pre-osteoblast cells at a concentration of 150,000 cells per suture piece and cells were allowed to attach for 24 hours. The suture pieces were then removed from the seeding media and placed in culture tubes with fresh media and incubated for 7 days. After 7 days post-seeding, cell counts were performed using a cell proliferation assay (Promega, MTS). The sutures displayed an average of 69071±16963 attached cells for un-irradiated controls and 208595±4873 attached cells for GCIB irradiated samples (p<0.0001).

In each suture evaluation, attachment and proliferation of cells on the GCIB irradiated suture samples was significantly higher than on the non-irradiated control samples. The effect was more pronounced in the GCIB irradiated samples receiving higher GCIB doses. The application of GCIB irradiation may also be used in combination with the techniques of coating (post GCIB irradiation) the sutures with proteins and/or attachment factors such as collagen, fibrin, or poly-L-lysine, if desired and appropriate. The GCIB irradiation of sutures may be employed to enhance the speed and degree of attachment of cells in-situ post-surgery. Alternatively, cells may be attached to the GCIB irradiated sutures ex-situ, prior to surgical implantation, to provide accelerated attachment and integration in situations where there is inherent Jack of vascularity at the surgical site and thus a lack or low rate of in-situ cellular attachment. By selectively irradiating portions of a suture (by masking or by direction of the irradiation beam), while leaving portions un-irradiated, the enhanced attachment effect can be limited to specific desired portions of any particular suture in situations where selective attachment may be desirable.

Cobalt-chrome Alloy Exemplary Embodiment

A cobalt-chrome alloy surface improvement is disclosed in another exemplary embodiment. Cobalt-chrome alloy is a material often employed in medical objects intended for implantation into a mammal, including vascular stents. Cobalt-chrome coupons were first cleaned in 70% isopropanol for 2 hours followed by 4 washes in double-distilled water for 15 minutes per wash, followed by 15 minutes under UV light in a biological hood. The cobalt-chrome alloy coupons were then either GCIB irradiated to a dose of $5 \times 10^{14}$ ions/cm$^2$ using an argon GCIB accelerated using 30 kV acceleration voltage or were left un-irradiated, as controls. The cobalt-chrome alloy coupons (both the irradiated samples and control samples) were then placed at the bottom of individual wells (3 control coupons and 3 GCIB irradiated coupons) of a 24-well Multiwell™ polystyrene plate (BD Falcon 351147). One ml of cell suspension (live mouse endothelial cells (EOMA cell line), 2,000 cells per ml) was seeded on each cobalt-chrome alloy coupon, with n=3 per condition (irradiated/not irradiated). The seeded cells were in suspended in Dulbecco's Modified Eagle Medium nutrient mixture (DMEM) supplemented with 10% fetal bovine serum (FBS) and 1% penicillin/streptomycin during incubation in a humidified incubator at 37° C.

Cells were allowed to attach for 24 hours on all the cobalt-chrome alloy coupons and then the media and any unattached cells were aspirated and fresh media was replaced and plates returned to the incubator. Cells were subsequently allowed to attach and proliferate on the surface of the cobalt-chrome alloy coupons while incubated for 10 additional days. At the end of 10 days, the cobalt-chrome alloy coupons were observed microscopically, verifying that essentially 100% cell attachment to the cobalt-chrome alloy coupon surface had occurred. Each coupon was removed from its well and media and placed in new wells that had not previously contained cells or media. Fresh media with MTS/PMS proliferation assay reagents per manufacturer's instructions (Promega, G5421) was used for cell assay and the cell assay was measured using a plate reader operating at a wavelength of 490 nm. Absorbance readings were converted to cell numbers based on a calibration curve previously generated with known cell numbers according to the MTS/PMS assay manufacturer's procedure to characterize the number of attached cells on each cobalt-chrome alloy coupon. The assay indicated that at the end of 10 days. EOMA cell proliferation and attachment on the unirradiated control coupons was 4,452±817 cells compared to 7,900±1, 164 cells on the GCIB irradiated coupons; (p<0.02).

An Accelerated Low Energy Neutral Beam Derived from an Accelerated GCIB

In some embodiments of the invention, a Neutral Beam derived from an accelerated gas cluster ion beam is employed to process insulating (and other sensitive) surfaces.

Figure 12:
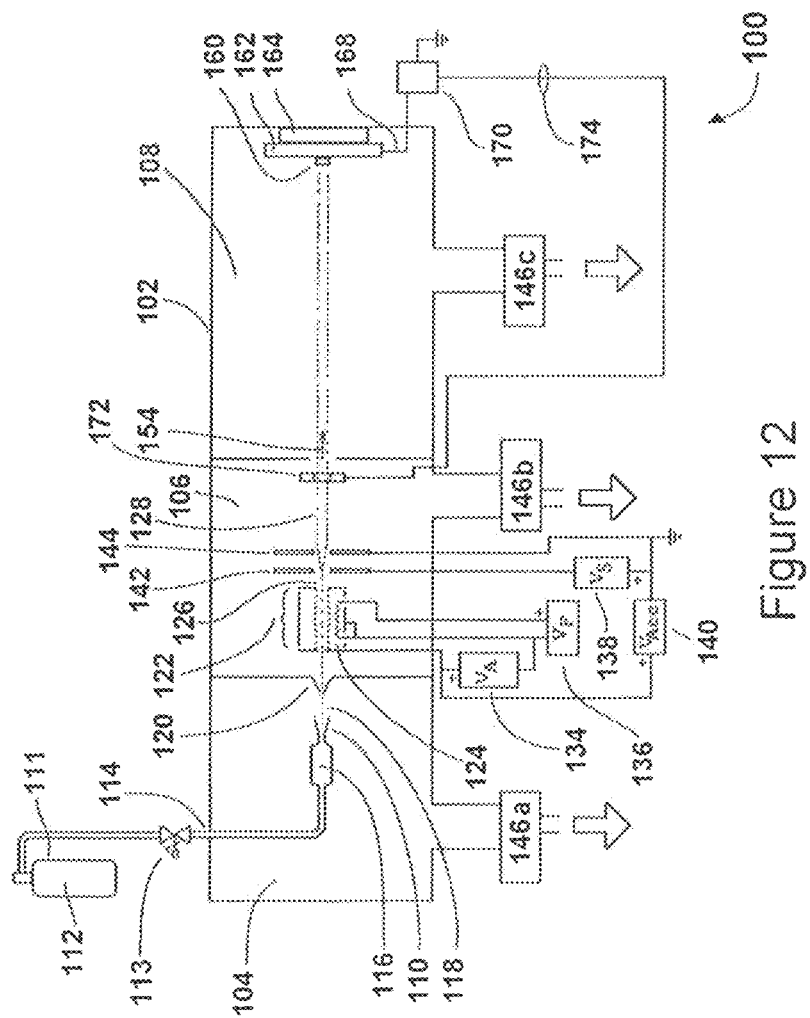
FIG. 12 is a schematic illustrating elements of a GCIB processing apparatus 100 for processing a workpiece using a GCIB.

Reference is now made to FIG. 12, which shows a schematic configuration for a GCIB processing apparatus 100. A low-pressure vessel 102 has three fluidly connected chambers: a nozzle chamber 104, an ionization/acceleration chamber 106, and a processing chamber 108. The three chambers are evacuated by vacuum pumps 146a. 146b, and 146c, respectively. A pressurized condensable source gas 112 (for example argon) stored in a gas storage cylinder 111 flows through a gas metering valve 113 and a feed tube 114 into a stagnation chamber 116. Pressure (typically a few atmospheres) in the stagnation chamber 116 results in ejection of gas into the substantially lower pressure vacuum through a nozzle 110, resulting in formation of a supersonic gas jet 118. Cooling, resulting from the expansion in the jet, causes a portion of the gas jet 118 to condense into clusters, each consisting of from several to several thousand weakly bound atoms or molecules. A gas skimmer aperture 120 is employed to control flow of gas into the downstream chambers by partially separating gas molecules that have not condensed into a cluster jet from the cluster jet. Excessive pressure in the downstream chambers can be detrimental by interfering with the transport of gas cluster ions and by interfering with management of the high voltages that may be employed for beam formation and transport. Suitable condensable source gases 112 include, but are not limited to argon and other condensable noble gases, nitrogen, carbon dioxide, oxygen, and many other gases and/or gas mixtures. After formation of the gas clusters in the supersonic gas jet 118, at least a portion of the gas clusters are ionized in an ionizer 122 that is typically an electron impact ionizer that produces electrons by thermal emission from one or more incandescent filaments 124 (or from other suitable electron sources) and accelerates and directs the electrons, enabling them to collide with gas clusters in the gas jet 118. Electron impacts with gas clusters eject electrons from some portion of the gas clusters, causing those clusters to become positively ionized. Some clusters may have more than one electron ejected and may become multiply ionized. Control of the number of electrons and their energies after acceleration typically influences the number of ionizations that may occur and the ratio between multiple and single ionizations of the gas clusters. A suppressor electrode 142, and grounded electrode 144 extract the cluster ions from the ionizer exit aperture 126, accelerate them to a desired energy (typically with acceleration potentials of from several hundred V to several tens of kV), and focuses them to form a GCIB 128. The region that the GCIB 128 traverses between the ionizer exit aperture 126 and the suppressor electrode 142 is referred to as the extraction region. The axis (determined at the nozzle 110), of the supersonic gas jet 118 containing gas clusters is substantially the same as the axis 154 of the GCIB 128. Filament power supply 136 provides filament voltage $V_F$ to heat the ionizer filament 124. Anode power supply 134 provides anode voltage $V_A$ to accelerate thermoelectrons emitted from filament 124 to cause the thermoelectrons to irradiate the cluster-containing gas jet 118 to produce cluster ions. A suppression power supply 138 supplies suppression voltage $V_S$ (on the order of several hundred to a few thousand volts) to bias suppressor electrode 142. Accelerator power supply 140 supplies acceleration voltage $V_{Acc}$ to bias the ionizer 122 with respect to suppressor electrode 142 and grounded electrode 144 so as to result in a total GCIB acceleration potential equal to $V_{Acc}$. Suppressor electrode 142 serves to extract ions from the ionizer exit aperture 126 of ionizer 122 and to prevent undesired electrons from entering the ionizer 122 from downstream, and to form a focused GCIB 128.

A workpiece 160, which may (for example) be a medical device, a semiconductor material, an optical element, or other workpiece to be processed by GCIB processing, is held on a workpiece holder 162, which disposes the workpiece in the path of the GCIB 128. The workpiece holder is attached to but electrically insulated from the processing chamber 108 by an electrical insulator 164. Thus, GCIB 128 striking the workpiece 160 and the workpiece holder 162 flows through an electrical lead 168 to a dose processor 170. A beam gate 172 controls transmission of the GCIB 128 along axis 154 to the workpiece 160. The beam gate 172 typically has an open state and a closed state that is controlled by a linkage 174 that may be (for example) electrical, mechanical, or electromechanical. Dose processor 170 controls the open/closed state of the beam gate 172 to manage the GCIB dose received by the workpiece 160 and the workpiece holder 162. In operation, the dose processor 170 opens the beam gate 172 to initiate GCIB irradiation of the workpiece 160. Dose processor 170 typically integrates GCIB electrical current arriving at the workpiece 160 and workpiece holder 162 to calculate an accumulated GCIB irradiation dose. At a predetermined dose, the dose processor 170 closes the beam gate 172, terminating processing when the predetermined dose has been achieved.

In the following description, for simplification of the drawings, item numbers from earlier figures may appear in subsequent figures without discussion. Likewise, items discussed in relation to earlier figures may appear in subsequent figures without item numbers or additional description. In such cases items with like numbers are like items and have the previously described features and functions and illustration of items without item numbers shown in the present figure refer to like items having the same functions as the like items illustrated in earlier numbered figures.

Figure 13:
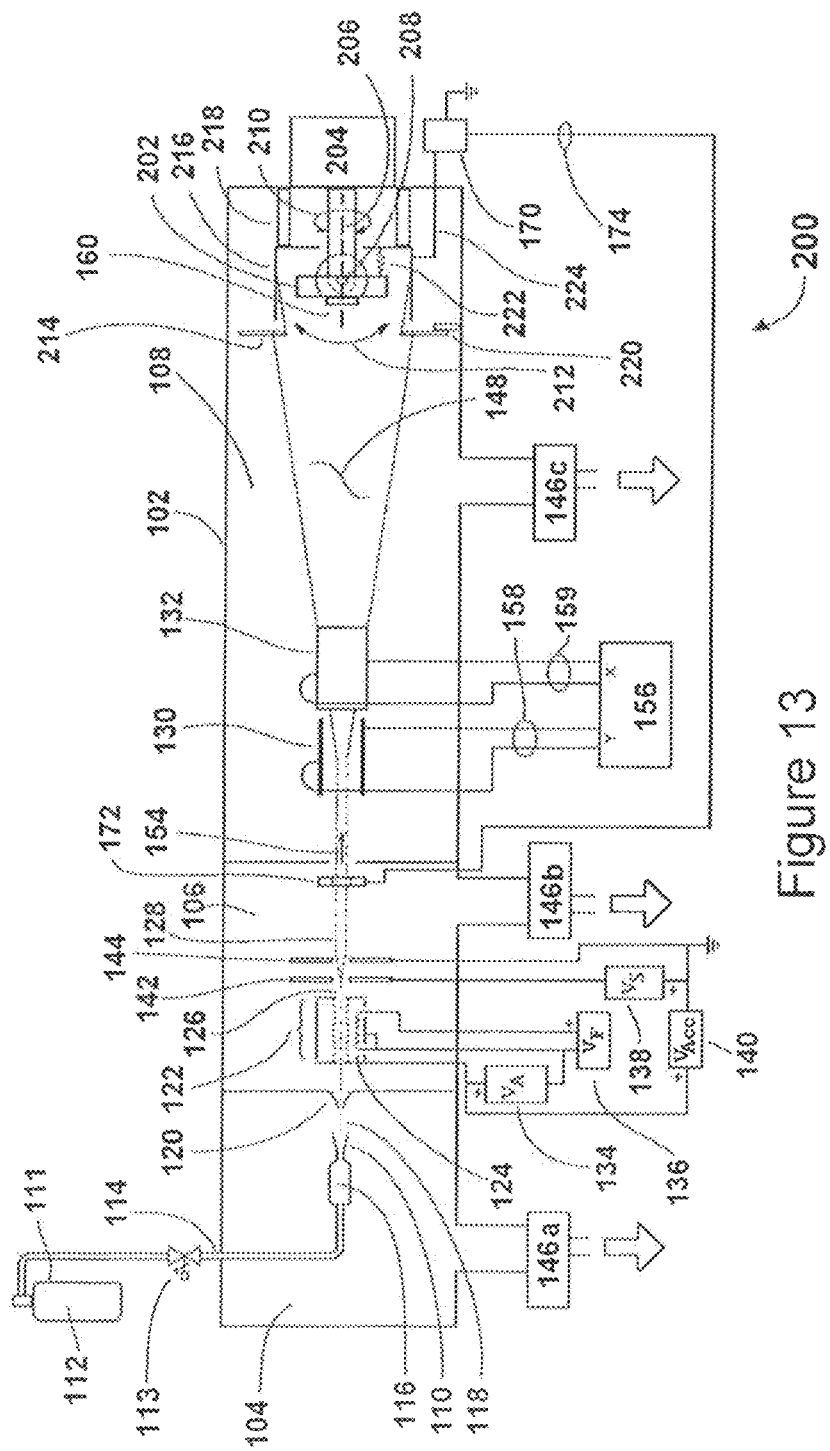
FIG. 13 is a schematic illustrating elements of another GCIB processing apparatus 200 for workpiece processing using a GCIB, wherein scanning of the ion beam and manipulation of the workpiece is employed.

FIG. 13 shows a schematic illustrating elements of another GCIB processing apparatus 200 for workpiece processing using a GCIB, wherein scanning of the ion beam and manipulation of the workpiece is employed. A workpiece 160 to be processed by the GCIB processing apparatus 200 is held on a workpiece holder 202, disposed in the path of the GCIB 128. In order to accomplish uniform processing of the workpiece 160, the workpiece holder 202 is designed to manipulate workpiece 160, as may be required for uniform processing.

Any workpiece surfaces that are non-planar, for example, spherical or cup-like, rounded, irregular, or other un-flat configuration, may be oriented within a range of angles with respect to the beam incidence to obtain optimal GCIB processing of the workpiece surfaces. The workpiece holder 202 can be fully articulated for orienting all non-planar surfaces to be processed in suitable alignment with the GCIB 128 to provide processing optimization and uniformity. More specifically, when the workpiece 160 being processed is non-planar, the workpiece holder 202 may be rotated in a rotary motion 210 and articulated in articulation motion 212 by an articulation/rotation mechanism 204. The articulation/rotation mechanism 204 may permit 360 degrees of device rotation about longitudinal axis 206 (which is coaxial with the axis 154 of the GCIB 128) and sufficient articulation about an axis 208 perpendicular to axis 206 to maintain the workpiece surface to within a desired range of beam incidence.

Under certain conditions, depending upon the size of the workpiece 160, a scanning system may be desirable to produce uniform irradiation of a large workpiece. Although often not necessary for GCIB processing, two pairs of orthogonally oriented electrostatic scan plates 130 and 132 may be utilized to produce a raster or other scanning pattern over an extended processing area. When such beam scanning is performed, a scan generator 156 provides X-axis scanning signal voltages to the pair of scan plates 132 through lead pair 159 and Y-axis scanning signal voltages to the pair of scan plates 130 through lead pair 158. The scanning signal voltages are commonly triangular waves of different frequencies that cause the GCIB 128 to be converted into a scanned GCIB 148, which scans the entire surface of the workpiece 160. A scanned beam-defining aperture 214 defines a scanned area. The scanned beam-defining aperture 214 is electrically conductive and is electrically connected to the low-pressure vessel 102 wall and supported by support member 220. The workpiece holder 202 is electrically connected via a flexible electrical lead 222 to a faraday cup 216 that surrounds the workpiece 160 and the workpiece holder 202 and collects all the current passing through the defining aperture 214. The workpiece holder 202 is electrically isolated from the articulation/rotation mechanism 204 and the faraday cup 216 is electrically isolated from and mounted to the low-pressure vessel 102 by insulators 218. Accordingly, all current from the scanned GCIB 148, which passes through the scanned beam-defining aperture 214 is collected in the faraday cup 216 and flows through electrical lead 224 to the dose processor 170. In operation, the dose processor 170 opens the beam gate 172 to initiate GCIB irradiation of the workpiece 160. The dose processor 170 typically integrates GCIB electrical current arriving at the workpiece 160 and workpiece holder 202 and faraday cup 216 to calculate an accumulated GCIB irradiation dose per unit area. At a predetermined dose, the dose processor 170 closes the beam gate 172, terminating processing when the predetermined dose has been achieved. During the accumulation of the predetermined dose, the workpiece 160 may be manipulated by the articulation/rotation mechanism 204 to ensure processing of all desired surfaces.

Figure 14:
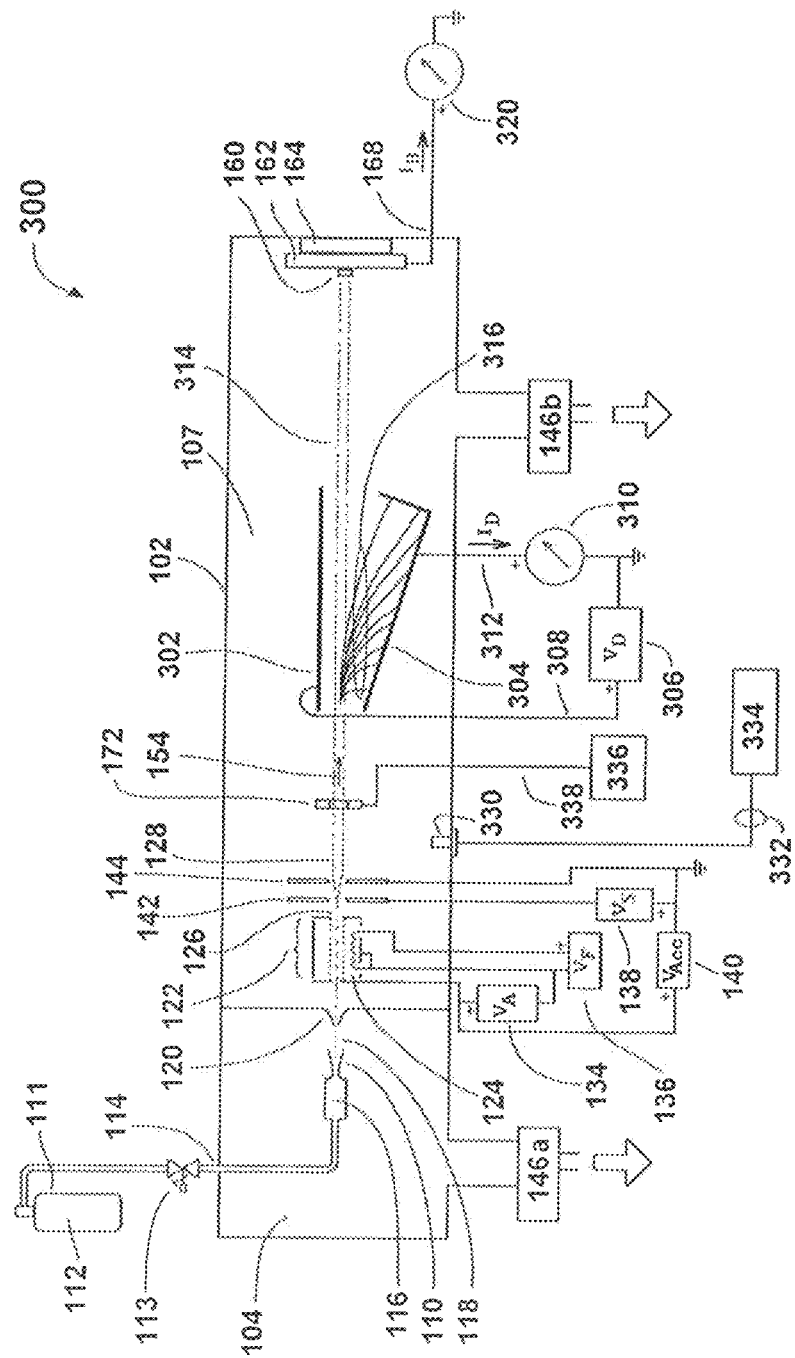
FIG. 14 is a schematic of a Neutral Beam processing apparatus 300 according to an embodiment of the invention, which uses electrostatic deflection plates to separate the charged and uncharged beams.

FIG. 14 is a schematic of a Neutral Beam processing apparatus 300 according to an embodiment of the invention, which uses electrostatic deflection plates to separate the charged and uncharged portions of a GCIB. A beamline chamber 107 encloses the ionizer and accelerator regions and the workpiece processing regions. The beamline chamber 107 has high conductance and so the pressure is substantially uniform throughout. A vacuum pump 146b evacuates the beamline chamber 107. Gas flows into the beamline chamber 107 in the form of clustered and unclustered gas transported by the gas jet 118 and in the form of additional unclustered gas that leaks through the gas skimmer aperture 120. A pressure sensor 330 transmits pressure data from the beamline chamber 107 through an electrical cable 332 to a pressure sensor controller 334, which measures and displays pressure in the beamline chamber 107. The pressure in the beamline chamber 107 depends on the balance of gas flow into the beamline chamber 107 and the pumping speed of the vacuum pump 146b. By selection of the diameter of the gas skimmer aperture 120, the flow of source gas 112 through the nozzle 110, and the pumping speed of the vacuum pump 146b, the pressure in the beamline chamber 107 equilibrates at a pressure, PB, determined by design and by nozzle flow. The GCIB flight path from grounded electrode 144 to workpiece holder 162, is for example, 100 cm. By design and adjustment PB may be approximately $6\times10^{-5}$ torr ($8\times10$ pascal). Thus the product of pressure and beam path length is approximately $6\times10^{-3}$ torr-cm (0.8 pascal-cm) and the gas target thickness for the beam is approximately $1.94\times10^{14}$ gas molecules per $cm^2$, which is observed to be effective for dissociating the gas cluster ions in the GCIB 128. $V_{Acc}$ may be for example 30 kV and the GCIB 128 is accelerated by that potential. A pair of deflection plates (302 and 304) is disposed about the axis 154 of the GCIB 128. A deflector power supply 306 provides a positive deflection voltage $V_D$ to deflection plate 302 via electrical lead 308. Deflection plate 304 is connected to electrical ground by electrical lead 312 and through current sensor/display 310. Deflector power supply 306 is manually controllable. $V_D$ may be adjusted from zero to a voltage sufficient to completely deflect the ionized portion 316 of the GCIB 128 onto the deflection plate 304 (for example a few thousand volts). When the ionized portion 316 of the GCIB 128 is deflected onto the deflection plate 304, the resulting current, $I_D$ flows through electrical lead 312 and current sensor/display 310 for indication. When $V_D$ is zero, the GCIB 128 is undeflected and travels to the workpiece 160 and the workpiece holder 162. The GCIB beam current $I_B$ is collected on the workpiece 160 and the workpiece holder 162 and flows through electrical lead 168 and current sensor/display 320 to electrical ground. $I_B$ is indicated on the current sensor/display 320. A beam gate 172 is controlled through a linkage 338 by beam gate controller 336. Beam gate controller 336 may be manual or may be electrically or mechanically timed by a preset value to open the beam gate 172 for a predetermined interval. In use, $V_D$ is set to zero, the beam current, $I_B$, striking the workpiece holder is measured. Based on previous experience for a given GCIB process recipe, an initial irradiation time for a given process is determined based on the measured current, $I_B$. $V_D$ is increased until all measured beam current is transferred from $I_B$ to $I_D$ and $I_D$ no longer increases with increasing $V_D$. At this point a Neutral Beam 314 comprising energetic dissociated components of the initial GCIB 128 irradiates the workpiece holder 162. The beam gate 172 is then closed and the workpiece 160 placed onto the workpiece holder 162 by conventional workpiece loading means (not shown). The beam gate 172 is opened for the predetermined initial radiation time. After the irradiation interval, the workpiece may be examined and the processing time adjusted as necessary to calibrate the duration of Neutral Beam processing based on the measured GCIB beam current $I_B$. Following such a calibration process, additional workpieces may be processed using the calibrated exposure duration.

The Neutral Beam 314 contains a repeatable fraction of the initial energy of the accelerated GCIB 128. The remaining ionized portion 316 of the original GCIB 128 has been removed from the Neutral Beam 314 and is collected by the grounded deflection plate 304. The ionized portion 316 that is removed from the Neutral Beam 314 may include monomer ions and gas cluster ions including intermediate size gas cluster ions. Because of the monomer evaporation mechanisms due to cluster heating during the ionization process, intra-beam collisions, background gas collisions, and other causes (all of which result in erosion of clusters) the Neutral Beam substantially consists of neutral monomers, while the separated charged particles are predominately cluster ions. The inventors have confirmed this by suitable measurements that include re-ionizing the Neutral Beam and measuring the charge to mass ratio of the resulting ions. As will be shown below, certain superior process results are obtained by processing workpieces using this Neutral Beam.

Figure 15:
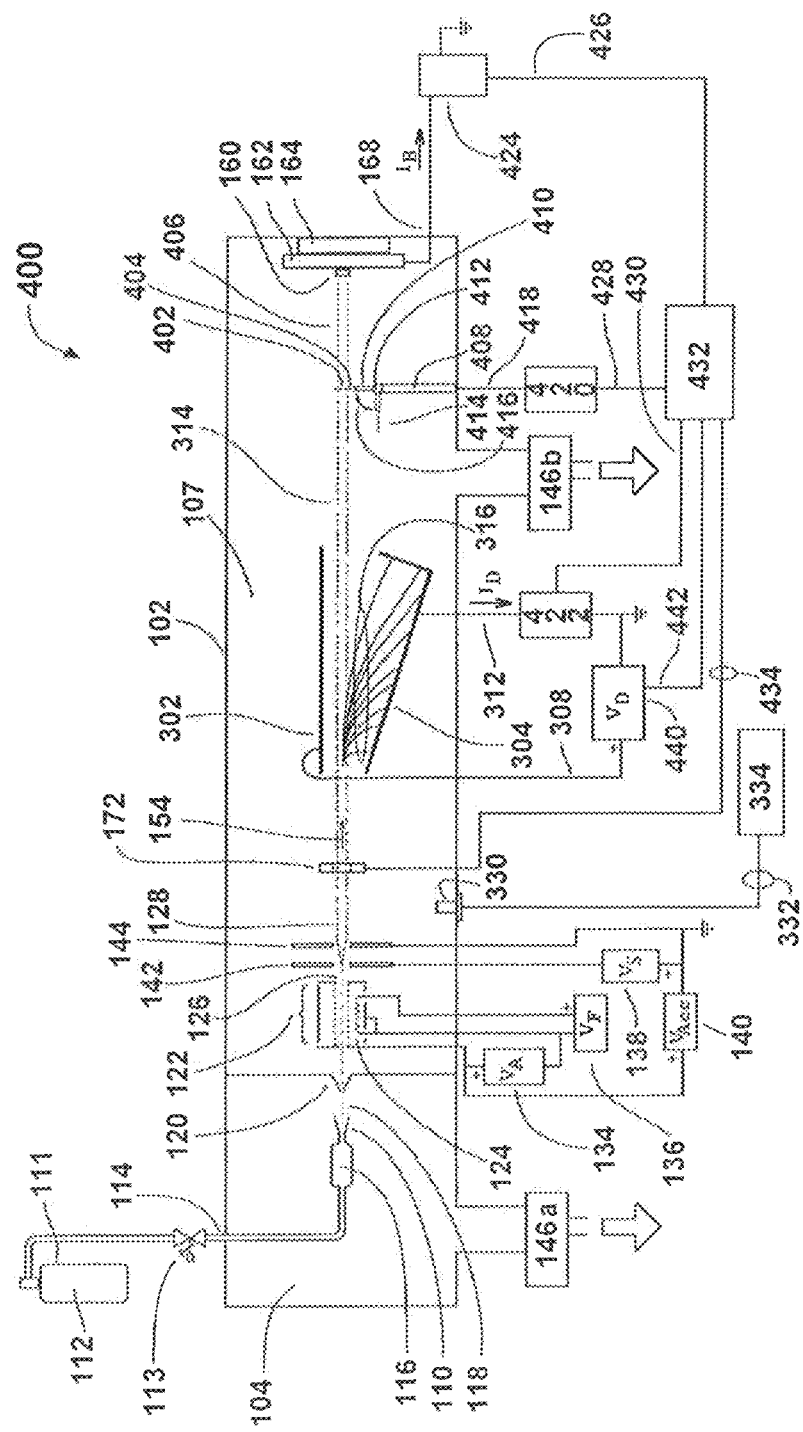
FIG. 15 is a schematic of a Neutral Beam processing apparatus 400 according to an embodiment of the invention, using a thermal sensor for Neutral Beam measurement.

FIG. 15 is a schematic of a Neutral Beam processing apparatus 400 according to an embodiment of the invention, which uses a thermal sensor for Neutral Beam measurement. A thermal sensor 402 attaches via low thermal conductivity attachment 404 to a rotating support arm 410 attached to a pivot 412. Actuator 408 moves thermal sensor 402 via a reversible rotary motion 416 between positions that intercept the Neutral Beam 314 or GCIB 128 and a parked position indicated by 414 where the thermal sensor 402 does not intercept any beam. When thermal sensor 402 is in the parked position (indicated by 414) the GCIB 128 or Neutral Beam 314 continues along path 406 for irradiation of the workpiece 160 and/or workpiece holder 162. A thermal sensor controller 420 controls positioning of the thermal sensor 402 and performs processing of the signal generated by thermal sensor 402. Thermal sensor 402 communicates with the thermal sensor controller 420 through an electrical cable 418. Thermal sensor controller 420 communicates with a dosimetry controller 432 through an electrical cable 428. A beam current measurement device 424 measures beam current $I_B$ flowing in electrical lead 168 when the GCIB 128 strikes the workpiece 160 and/or the workpiece holder 162. Beam current measurement device 424 communicates a beam current measurement signal to dosimetry controller 432 via electrical cable 426. Dosimetry controller 432 controls setting of open and closed states for beam gate 172 by control signals transmitted via linkage 434. Dosimetry controller 432 controls deflector power supply 440 via electrical cable 442 and can control the deflection voltage $V_D$ between voltages of zero and a positive voltage adequate to completely deflect the ionized portion 316 of the GCIB 128 to the deflection plate 304. When the ionized portion 316 of the GCIB 128 strikes deflection plate 304, the resulting current $I_D$ is measured by current sensor 422 and communicated to the dosimetry controller 432 via electrical cable 430. In operation dosimetry controller 432 sets the thermal sensor 402 to the parked position 414, opens beam gate 172, sets $V_D$ to zero so that the full GCIB 128 strikes the workpiece holder 162 and/or workpiece 160. The dosimetry controller 432 records the beam current $I_B$ transmitted from beam current measurement device 424. The dosimetry controller 432 then moves the thermal sensor 402 from the parked position 414 to intercept the GCIB 128 by commands relayed through thermal sensor controller 420. Thermal sensor controller 420 measures the beam energy flux of GCIB 128 by calculation based on the heat capacity of the sensor and measured rate of temperature rise of the thermal sensor 402 as its temperature rises through a predetermined measurement temperature (for example 70 degrees C.) and communicates the calculated beam energy flux to the dosimetry controller 432 which then calculates a calibration of the beam energy flux as measured by the thermal sensor 402 and the corresponding beam current measured by the beam current measurement device 424. The dosimetry controller 432 then parks the thermal sensor 402 at parked position 414, allowing it to cool and commands application of positive $V_D$ to deflection plate 302 until all of the current $I_D$ due to the ionized portion of the GCIB 128 is transferred to the deflection plate 304. The current sensor 422 measures the corresponding $I_D$ and communicates it to the dosimetry controller 432. The dosimetry controller also moves the thermal sensor 402 from parked position 414 to intercept the Neutral Beam 314 by commands relayed through thermal sensor controller 420. Thermal sensor controller 420 measures the beam energy flux of the Neutral Beam 314 using the previously determined calibration factor and the rate of temperature rise of the thermal sensor 402 as its temperature rises through the predetermined measurement temperature and communicates the Neutral Beam energy flux to the dosimetry controller 432. The dosimetry controller 432 calculates a neutral beam fraction, which is the ratio of the thermal measurement of the Neutral Beam 314 energy flux to the thermal measurement of the full GCIB 128 energy flux. Under typical operation, a neutral beam fraction of about 5% to about 95% is achieved. Before beginning processing, the dosimetry controller 432 also measures the current, $I_D$, and determines a current ratio between the initial values of $I_B$ and $I_D$. During processing, the instantaneous $T_D$ measurement multiplied by the initial $I_B/I_D$ ratio may be used as a proxy for continuous measurement of the $I_B$ and employed for dosimetry during control of processing by the dosimetry controller 432. Thus the dosimetry controller 432 can compensate any beam fluctuation during workpiece processing, just as if an actual beam current measurement for the full GCIB 128 were available. The dosimetry controller uses the neutral beam fraction to compute a desired processing time for a particular beam process. During the process, the processing time can be adjusted based on the calibrated measurement of $I_D$ for correction of any beam fluctuation during the process.

Polymer Exemplary Embodiments Using an Accelerated Low Energy Neutral Beam

In addition to the in vitro increase in osteoblast cell proliferation on GCIB-irradiated PEEK surfaces shown in FIG. 8, in vivo tests show that bone growth at a Neutral Beam-irradiated PEEK surface proceeds more readily than on an un-irradiated PEEK control surface. To demonstrate this effect, a rat critical size calvaria defect model was employed. In accord with the U.S. Animal Welfare Act and its amendments, laboratory Rattus norvegicus (Sprague-Dawley strain) rats were anesthesized, and using sterile technique, a drill with a 3.0 mm trephine was used to remove a circular disk of bone from each rat calvarium, forming a critical size defect (defect of a size that will not heal naturally during the lifetime of the animal). Circular PEEK disks 3.125 mm diameter and 1 mm thick were implanted to fill the defect site, and the soft tissue and skin closed in appropriate layers. The rats were divided into control and test groups. The control group received sterile un-irradiated PEEK disk implants. The test group received sterile PEEK disk implants that had been Neutral Beam-irradiated on both 3.125 mm circular surfaces, but not on the 1 mm thick cylindrical edges. Data on the control and test groups are shown in Table 3. Following surgical implant, the wounds were allowed to heal for 4 weeks. Following 4 weeks, the rats (both groups) were euthanized and tissue samples collected for histological examination and evaluation. Un-decalcified, intact calvaria with (control and test) implant sites were resin embedded and micro-ground to form transverse sections. The sections were stained using conventional hematoxylin and eosin histology techniques, and were examined microscopically to evaluate formation of bone growth at the implant sites.

TABLE 3

| Group | Surgical implant | Number of rats | Number of implant sites per Group | Post-implant recovery interval (weeks) |
| --- | --- | --- | --- | --- |
| 1 | Un-irradiated PEEK (control group) | 6 | 6 | 4 |
| 2 | Neutral beam-irradiated PEEK (test group) | 6 | 6 | 4 |

In the test group, 5 of 6 members of the group exhibited sparse to moderate bone coverage of the outer surface of the Neutral Beam-irradiated PEEK disk. For the control group, 2 of 6 members exhibited only sparse bone growth on the outer surface of the un-irradiated PEEK disk.

For the test group, Group 2, Neutral Beam irradiation was performed using an apparatus similar to that of FIG. 15. Referring to FIG. 15, an accelerated (using 30 kV acceleration potential. $V_{Acc}$) argon GCIB 128 was formed and directed at the PEEK disk (workpiece 160). The distance (beam path length) from ionizer exit aperture 126 to the workpiece 160 was approximately 61 cm. The pressure in the low pressure vessel 102 was maintained at approximately $6.7 \times 10^{-5}$ torr and the background gas forming that pressure was substantially argon. The product of pressure times the beam path length was thus approximately $4.09 \times 10^{-3}$ torr-cm and the corresponding argon gas target thickness for the region between the ionizer exit aperture 126 and the workpiece 160 was therefore approximately $1.32 \times 10^{14}$ argon gas monomers/cm$^2$, which is observed to be effective for essentially completely dissociating gas cluster ions in the GCIB 128. A pair of electrostatic deflection plates (302 and 304) disposed about the axis 154 of the GCIB 128 was used to completely deflect all charged particles out of the beam axis 154, forming the Neutral Beam 314, which was essentially fully dissociated. Thus the Neutral Beam 314 was an accelerated monomer neutral argon beam. Dosimetry as done using a thermal sensor 402 to calibrate the total Neutral Beam dose delivered to each circular side of the PEEK disk such that each side received a Neutral Beam deposited energy equivalent to that energy which would be deposited by a $5 \times 10^{14}$ ion/cm$^2$ irradiation by an accelerated (30 kV) GCIB 128 including both the charged and uncharged particles (without neutralization by charge separation).

Figure 16A:
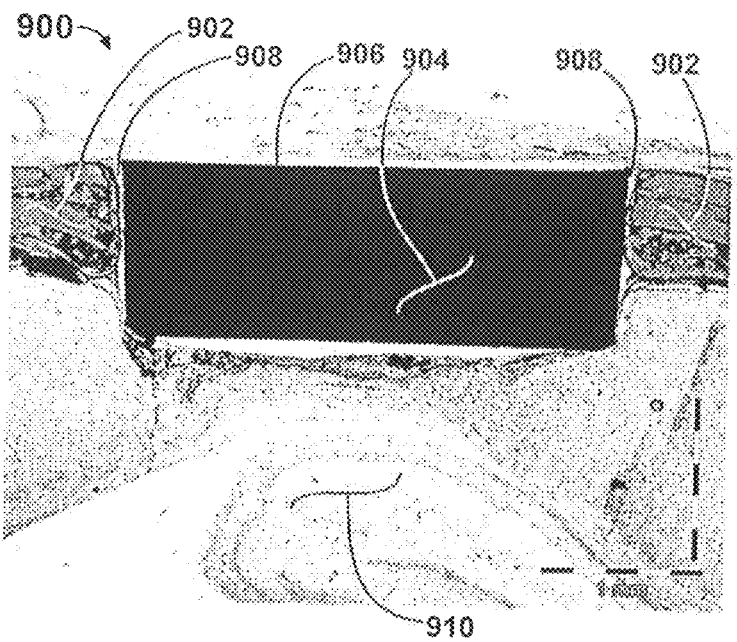
FIGS. 16a and 16b are optical micrographs 900 and 920 of histological transverse sections (FIG. 16a) control and (FIG. 16b) Neutral Beam irradiated PEEK disks surgically implanted in rat calvaria, showing relative degrees of growth of new bone four weeks post-implant.

FIG. 16a is an optical micrograph 900 of a transverse section representative of the samples from Group 1, the control group, showing the un-irradiated PEEK disk 904 in its rat calvarium surgical implant site after 4 weeks post-implant healing. Original calvarium bone 902 has a circular opening seen in transverse section and filled by un-irradiated PEEK disk 904. The un-irradiated PEEK disk 904 has an interface 908 with the circular opening in the original calvarium bone 902. The un-irradiated PEEK disk 904 has an outer surface 906. No significant regrowth of bone is observed at outer surface 906. Cerebral tissue 910 is also seen in the micrograph.

Figure 16B:
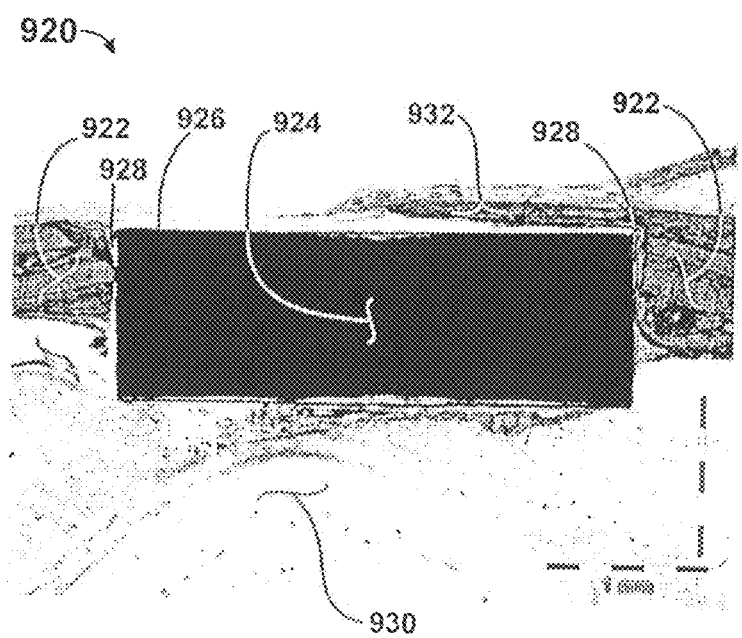

FIG. 16b is an optical micrograph 920 of a transverse section representative of the samples from Group 2, the test group, showing the Neutral Beam-irradiated PEEK disk 924 in its rat calvarium surgical implant site after 4 weeks post-implant healing. Original calvarium bone 922 has a circular opening seen in transverse section and filled by Neutral Beam-irradiated PEEK disk 924. The Neutral Beam-irradiated PEEK disk 924 has an interface 928 with the circular opening in the original calvarium bone 922. The Neutral Beam-irradiated PEEK disk 924 has a Neutral Beam-irradiated outer surface 926. Regrowth 932 of bone is observed at outer surface 926. Cerebral tissue 930 is also seen in the micrograph.

A second polymer surface improvement by Neutral Beam irradiation is now disclosed in another exemplary embodiment. Polytetrafluoroethylene (PTFE) substrates in the form of coupons (10 mm×10 mm×1.5 mm thick) were irradiated using a Neutral Beam derived from an argon GCIB accelerated using a 30 kV $V_{Acc}$. Dosimetry was done using a thermal sensor to calibrate the total Neutral Beam dose delivered to each irradiated PTFE coupon such that one side of each irradiated PTFE coupon received a Neutral Beam deposited energy equivalent to that energy which would be deposited by a $5\times10^{14}$ ion/cm$^2$ irradiation by an accelerated (30 kV) GCIB including both the charged and uncharged particles (without neutralization by charge separation). Control coupons were left un-irradiated.

The cyto-compatibility and bioactivity of PTFE are improved by Neutral Beam irradiation, making the material more suitable for surgical implant in situations where cell attachment and integration is desired. PTFE coupons were pre-cleaned by placing them in 70% isopropyl alcohol for 2 hours, followed by 4 washes in double-distilled water for 15 minutes per wash, followed by UV sterilization. The PTFE coupons were then irradiated by Neutral Beam (or left unirradiated as controls), and then UV sterilized again. The PTFE coupons were placed in individual wells of 24-well sterile polystyrene plates (non tissue culture treated to avoid having cells attach to the plastic of the plates).

Live mouse endothelial cells (EOMA cell line) were seeded onto the PTFE coupons (3 control coupons and 6 irradiated coupons) at a concentration of 20,000 cells per ml per well and allowed to attach for 24 hours in Dulbecco's Modified Eagle Medium nutrient mixture (DMEM) supplemented with 10% fetal bovine serum (FBS) and 1% penicillin/streptomycin during incubation in a humidified incubator at 37° C. Cells were allowed to attach for 24 hours on all the PTFE coupons and then the media and any unattached cells were aspirated and fresh media with MTS/PMS proliferation assay reagents per manufacturer's instructions (Promega, G5421) was used for cell assay. The the cell assay was measured using a plate reader operating at a wavelength of 490 nm. Absorbance readings were converted to cell numbers based on a calibration curve previously generated with known cell numbers according to the MTS/PMS assay manufacturer's procedure to characterize the number of attached cells on each PTFE coupon. Following each assay of the irradiated PTFE samples with attached cells were examined to confirm cell attachment and cell growth on the irradiated PTFE surfaces.

For the unirradiated PTFE control coupons the average assayed cell attachment was 17 cells per coupon (with a standard deviation of 306). For the irradiated PTFE coupons, the average assayed cell attachment was 4908 cells (standard deviation was 1766). The difference between the control and irradiated groups was statistically significant (p=0.0008), as determined by applying a heteroscedastic T-test. 24 hour EOMA cell attachment on the PTFE was dramatically improved in the Neutral Beam irradiated samples compared to the un-irradiated samples.

Titania Exemplary Embodiment Using an Accelerated Low Energy Neutral Beam

In addition to the surface improvement results on titanium surfaces discussed above for GCIB irradiation (and shown in FIGS. 1 through 3), in an additional exemplary embodiment, an accelerated Neutral Beam derived from an accelerated argon GCIB is disclosed as causing titania surface improvement. Titanium is a material often employed in medical objects intended for implantation into a mammal. Titanium coupons (CP grade 4, 6 mm diameter×1 mm thick) having a machined surface were first cleaned in 70% isopropanol for 2 hours and then air dried in a bio-safety cabinet overnight. It is understood that the cleaned titanium samples, as with any titanium that has been exposed to normal atmospheric conditions, likely has a very thin native titania surface coating, which may be incomplete and may be imperfect. The titanium coupons were then either irradiated using a Neutral Beam derived from an argon GCIB accelerated with 30 kV $V_{Acc}$. GCIB irradiated to a dose of $5\times10^{14}$ ions/cm$^2$ using an argon GCIB accelerated using 30 kV acceleration voltage or were left un-irradiated, as controls. Dosimetry was done using a thermal sensor to calibrate the total Neutral Beam dose delivered to each irradiated titanium coupon such that one side of each coupon received a Neutral Beam deposited energy equivalent to that energy which would be deposited by a $5\times10^{14}$ ion/cm$^2$ irradiation by an accelerated (30 kV) GCIB including both the charged and uncharged particles (without neutralization by charge separation).

The titanium coupons (both the irradiated samples, n=8 per time point, and control samples, n=8 per time point) were then placed at the bottom of individual wells of a 48-well sterile polystyrene plates (non tissue culture treated to avoid having cells attach to the plastic of the plates). 2000 human osteoblast cells were seeded on the surfaces of the titanium coupons in 0.5 ml of (Invitrogen Corp.) Dulbecco's Modified Eagle Medium nutrient mixture (DMEM) supplemented with 10% fetal bovine serum (FBS) and incubated in a humidified incubator at 37° C. and 5% $CO_2$ in air. Media was changed every 3-4 days. At time points of 1 day, 7 days, and 14 days, media samples were removed and cells were assayed using CellTiter 96® AQueous Cell Proliferation Assay from Promega used according to the manufacturer's instructions, with the measurement made using a Dynex OpsysMR plate reader at 490 nm wavelength. Absorbance measurements were converted to cell counts using a standard calibration curve based on known cell counts. The cell count results and their mean values are tabulated in Table 4.

TABLE 4

| | Control Samples | | | Neutral Beam Irradiated Samples | | |
|---|---|---|---|---|---|---|
| Sample # | Day 1 cell counts | Day 7 cell counts | Day 14 cell counts | Day 1 cell counts | Day 7 cell counts | Day 14 cell counts |
| 1 | 750.0 | 11666.7 | 7666.7 | 1583.3 | 19583.3 | 33083.3 |
| 2 | 1250.0 | 7250.0 | 8000.0 | 1916.7 | 14916.7 | 34833.3 |
| 3 | 1166.7 | 9666.7 | 4083.3 | 1833.3 | 12333.3 | 28000.0 |
| 4 | 1416.7 | 10500.0 | 10750.0 | 1166.7 | 12833.3 | 33250.0 |
| 5 | 1083.3 | 11500.0 | 8750.0 | 1083.3 | 19416.7 | 34666.7 |

TABLE 4-continued

| | Control Samples | | | Neutral Beam Irradiated Samples | | |
|---|---|---|---|---|---|---|
| Sample # | Day 1 cell counts | Day 7 cell counts | Day 14 cell counts | Day 1 cell counts | Day 7 cell counts | Day 14 cell counts |
| 6 | 1416.7 | 6750.0 | 8500.0 | 1166.7 | 14916.7 | 34333.3 |
| 7 | 1000.0 | 9750.0 | 3833.3 | 1583.3 | 12833.3 | 26666.7 |
| 8 | 1083.3 | 10583.3 | 11000.0 | 1333.3 | 12583.3 | 33583.3 |
| Mean | 1145.8 | 9708.3 | 7822.9 | 1458.3 | 14927.1 | 32302.1 |

Table 5 summarizes statistics of the comparison of the control samples to the irradiated samples. The p-values were obtained by applying a paired T-test.

TABLE 5

| | Control Samples | | Neutral Beam Irradiated Samples | | (Control vs. irradiated) |
|---|---|---|---|---|---|
| Time | Mean | σ | Mean | σ | p Value |
| Day 1 | 1145.8 | 221.6 | 1458.3 | 318.1 | 0.082 |
| Day 7 | 9708.3 | 1821.9 | 14927.1 | 2995.9 | 0.0014 |
| Day 14 | 7822.9 | 2670.9 | 32302.1 | 3151.9 | $2 \times 10^{-9}$ |

Results showed that osteoblast cells adhered to and proliferated on the irradiated titanium coupons preferentially to the un-irradiated control coupons with an increasing statistical confidence after 7 and 14 days.

In the several embodiments disclosed above, the method of this invention may further include combination with other previously known methods for improving the surfaces and/or for enhancing bioactivity and integration including, without limitation, sandblasting, acid etching, plasma spraying of coatings, $CO_2$ laser smoothing and various forms of cleaning, including mechanical, ultrasonic, plasma, and chemical cleaning techniques, the use of surfactants or the application of films or coatings having different wettability characteristics, UV treatment, UV and ozone treatment, covalently attaching poly(ethylene glycol) (PEG), and the application of protein products such as the antibody anti-CD34 and/or arginine-glycine-aspartate peptides (RGD peptides) and/or collagen and/or albumin. Such combinations are intended to be encompassed within the scope of the invention.

Although the invention has been described for exemplary purposes as employing titanium foil, glass, polystyrene, PTFE, PEEK, quartz, sapphire, PETE fabric, and cobalt-chrome alloy surfaces, it is understood that objects for medical implant formed from titanium and/or titanium alloys (with or without oxide coatings), cobalt-chrome alloys, cobalt-chrome-molybdenum alloys, tantalum, tantalum alloys, various other metals and metal alloys, plastic or polymer or co-polymer materials including polyethylene and other inert plastics, solid resin materials, glassy materials, woven, knitted, and non-woven polymeric/co-polymeric fabrics, biological materials such as bone, collagen, silk and other natural fibers, various ceramics including titania, and other materials that may be suitable for the application and that are appropriately biocompatible. Although the invention has been described with respect to various embodiments and applications in the field of objects for medical implantation, it is understood by the inventors that its application is not limited to that field and that the concepts of GCIB irradiation and accelerated Neutral Beam irradiation of surfaces to make them more conducive to cellular growth, attachment, and attachment has broader application in fields that will be apparent to those skilled in the art. Such broader applications are intended to be encompassed within the scope of this invention.

Although the invention has been described for exemplary purposes as using a Neutral Beam derived from an accelerated gas cluster ion beam for processing the charge sensitive insulating materials, PEEK and PTFE, it is understood by the inventors that benefits obtained by application of such Neutral Beam surface processing is not limited to the PEEK and PTFE materials and that it offers improvements for many charge sensitive materials and electrically insulating or high resistivity materials, including without limitation, glass, polystyrene. PTFE, PEEK, quartz, sapphire, and PETE fabric. It is understood that objects for medical implant benefit from Neutral Beam processing when formed from plastic or polymer or co-polymer materials including polyethylene and other inert plastics, solid resin materials, glassy materials, woven, knitted, and non-woven polymeric/co-polymeric fabrics, biological materials such as bone, collagen, silk and other natural fibers, various ceramics including titania, as well as other materials that may be suitable for the application and that are appropriately biocompatible and which are sensitive to charging or charge damage by ion beams.

Furthermore, it has been shown that materials that are not electrically insulating, nor charge sensitive can derive surface improvements by processing with accelerated Neutral Beams, as shown by the exemplary results shown for Neutral Beam irradiation of titania. It is understood by the inventors that surface processing of a wide variety of materials, electrically conductive or insulating benefit from Neutral Beam processing and from GCIB processing, and it is intended that the scope of the invention includes processing by GCIB and by Neutral Beams derived from GCIB of a wide variety of surfaces to improve their cyto-compatibility and biocompatibility. It should be realized that this invention is also capable of a wide variety of further and other embodiments within the spirit and scope of the invention and the claims.

What is claimed is:

1. An article having a surface region comprising one or more materials selected from the group consisting of titania, titanium, an alloy of titanium, and polytetrafluoroethylene (PTFE) with attached cells made by a method comprising the steps of:
    selecting at least a portion of a surface of the article for attaching cells;
    forming an accelerated and focused Neutral Beam in a reduced-pressure chamber, including forming a gas-cluster ion-beam comprising ionized gas clusters in the reduced-pressure chamber;
    accelerating and focusing the gas-cluster ion-beam along a beam path;
    at least partially dissociating gas clusters in the gas-cluster ion-beam along the beam path by increasing the range of velocities of ions in the accelerated gas cluster ion beam wherein the Neutral Beam is essentially free of intermediate size clusters;
    at least partially neutralizing the gas cluster ion-beam;
    separating ionized particles from the at least partially neutralized gas-cluster ion-beam to form the accelerated Neutral Beam;
    introducing said article into said reduced-pressure chamber before or after pressure reduction therein;
    irradiating said at least a portion of said surface with the accelerated and focused Neutral Beam, wherein the at least a portion of said surface has a characteristic defined by irradiation from an accelerated and focused Neutral Beam;

removing said article from said reduced-pressure chamber; and exposing said at least a portion of said surface to living cells.

2. An article having a surface region with modified hydrophilicity made by a method comprising the steps of:

selecting at least a portion of the surface of the article;

forming an accelerated and focused Neutral Beam in a reduced-pressure chamber, including forming a gas-cluster ion-beam comprising ionized gas clusters in the reduced-pressure chamber;

accelerating and focusing the gas-cluster ion-beam along a beam path;

at least partially dissociating gas clusters in the gas-cluster ion-beam along the beam path by increasing the range of velocities of ions in the accelerated gas cluster ion beam wherein the Neutral Beam is essentially free of intermediate size clusters;

at least partially neutralizing the gas cluster ion-beam;

separating ionized particles from the at least partially neutralized gas-cluster ion-beam to form the accelerated Neutral Beam;

introducing said article into said reduced-pressure chamber before or after pressure reduction therein;

irradiating said at least a portion of said surface with the accelerated and focused Neutral Beam, wherein the at least a portion of said surface has characteristic smoothness and modified hydrophilicity defined by irradiation from an accelerated and focused Neutral Beam; and removing said article from said reduced-pressure chamber.

3. The article of claim 2, wherein the at least a portion of a surface comprises a material, a film, or a coating selected from the group consisting of a polymer, a dielectric, an electrically insulating, and a high electrical resistivity material.

4. The article of claim 2, wherein the at least a portion of a surface comprises a material selected from the group consisting of glass, polymer, and ceramic.

5. The article of claim 2, wherein the at least a portion of a surface comprises a material selected from the group consisting of titania, titanium, an alloy of titanium, polytetrafluoroethylene, and polyether ether ketone.

6. A method of improving the hydrophilicity of at least a portion of a surface of an object, the method comprising:

forming an accelerate and focused Neutral Beam in a reduced-pressure chamber, including forming a gas-cluster ion-beam comprising ionized gas clusters in the reduced-pressure chamber;

accelerating and focusing the gas-cluster ion-beam along a beam path;

at least partially dissociating gas clusters in the gas-cluster ion-beam along the beam path by increasing the range of velocities of ions in the accelerated gas cluster ion beam wherein the neutral Beam is essentially free of intermediate size clusters;

at least partially neutralizing the gas cluster ion-beam;

separating ionized particles from the at least partially neutralized gas-cluster ion-beam to form the accelerated Neutral Beam;

introducing said object into said reduced-pressure chamber before or after pressure reduction therein;

irradiating said at least a portion of said surface with the accelerated Neutral Beam; and removing said object from said reduced-pressure chamber.

7. The method of claim 6, wherein the at least a portion of a surface comprises a material, a film, or a coating selected from the group consisting of a polymer, a dielectric, an electrically insulating, and a high electrical resistivity material.

8. The method of claim 6, wherein the at least a portion of a surface comprises a material selected from the group consisting of glass, polymer, and ceramic.

9. The method of claim 6, wherein the at least a portion of a surface comprises a material selected from the group consisting of titania, titanium, an alloy of titanium, polytetrafluoroethylene, polyether ether ketone, a metal, and a metal alloy.

10. The article of claim 2, wherein hydrophilicity of the at least a portion of said surface is increased.

11. The article of claim 2, wherein the at least a portion of a surface comprises a material selected from the group consisting of a metal, and a metal alloy.

12. The article of claim 1, wherein the at least a portion of said surface has a characteristic defined by irradiation from an accelerated and focused Neutral Beam consisting essentially of neutral monomers.

13. The article of claim 2, wherein the at least a portion of said surface has characteristic smoothness and modified hydrophilicity defined by irradiation from an accelerated and focused Neutral Beam consisting essentially of neutral monomers.

* * * * *